(12) United States Patent
Sacco et al.

(10) Patent No.: US 7,803,887 B2
(45) Date of Patent: *Sep. 28, 2010

(54) METALLOCENE COMPOUNDS

(75) Inventors: Marco Sacco, Ferrara (IT); Ilya Nifant'ev, Moscow (RU); Pavel Ivchenko, Moscow (RU); Vladimir Bagrov, Moscow (RU); Francesca Focante, Ancona (IT)

(73) Assignee: Basell Polyolefine GmbH, Wesseling (DE)

( * ) Notice: Subject to any disclaimer, the term of this patent is extended or adjusted under 35 U.S.C. 154(b) by 140 days.

This patent is subject to a terminal disclaimer.

(21) Appl. No.: 11/886,617

(22) PCT Filed: Mar. 15, 2006

(86) PCT No.: PCT/EP2006/060772

§ 371 (c)(1),
(2), (4) Date: Sep. 18, 2007

(87) PCT Pub. No.: WO2006/097500

PCT Pub. Date: Sep. 21, 2006

(65) Prior Publication Data

US 2009/0221772 A1    Sep. 3, 2009

Related U.S. Application Data

(60) Provisional application No. 60/710,293, filed on Aug. 22, 2005.

(30) Foreign Application Priority Data

| Mar. 18, 2005 | (EP) | .................. 05102189 |
| Aug. 5, 2005 | (EP) | .................. 05107248 |
| Dec. 22, 2005 | (EP) | .................. 05112766 |

(51) Int. Cl.
*C08F 4/64* (2006.01)
*C08F 4/76* (2006.01)
*C08F 4/52* (2006.01)
*C07F 17/00* (2006.01)

(52) U.S. Cl. ............ 526/161; 526/172; 526/160; 526/170; 526/943; 526/941; 526/127; 526/128; 526/129; 526/348; 526/351; 502/103; 502/152; 556/53

(58) Field of Classification Search .......... 556/53, 556/51, 52; 526/161, 172; 502/103
See application file for complete search history.

(56) References Cited

U.S. PATENT DOCUMENTS

| 4,178,272 | A | 12/1979 | Meyer, Jr. et al. |
| 5,698,487 | A | 12/1997 | Sacchetti et al. |
| 5,770,664 | A | 6/1998 | Okumura et al. |
| 5,770,753 | A | 6/1998 | Küber et al. |
| 5,786,432 | A | 7/1998 | Küber et al. |
| 5,840,644 | A | 11/1998 | Küber et al. |
| 6,051,727 | A | 4/2000 | Küber et al. |
| 6,242,544 | B1 | 6/2001 | Küber et al. |
| 6,255,506 | B1 | 7/2001 | Küber et al. |
| 6,306,996 | B1 | 10/2001 | Cecchin et al. |
| 6,399,533 | B2 | 6/2002 | Sacchetti et al. |
| 6,444,833 | B1 | 9/2002 | Ewen et al. |
| 6,492,539 | B1 | 12/2002 | Bingel et al. |
| 6,559,252 | B1 | 5/2003 | Horton et al. |
| 6,608,224 | B2 | 8/2003 | Resconi et al. |
| 6,635,779 | B1 | 10/2003 | Ewen et al. |
| 6,841,501 | B2 | 1/2005 | Resconi et al. |

(Continued)

FOREIGN PATENT DOCUMENTS

DE    19917985    10/2000

(Continued)

OTHER PUBLICATIONS

C. Carman et al., "Monomer Sequence Distribution in Ethylene-Propylene Rubber Measured by $^{13}$C NMR. 3. Use of Reaction Probability Model," *Macromolecules*, vol. 10(3), p. 536-544 (1977).

(Continued)

*Primary Examiner*—Rip A. Lee
(74) *Attorney, Agent, or Firm*—Jarrod N. Raphael; Jonathan L. Schuchardt

(57) ABSTRACT

A bridged metallocene compound of formula (I) wherein: M is a transition metal; X, is a hydrogen atom, a halogen atom, or a hydrocarbon group optionally containing hetematoms; L is a divalent bridging group; $R^1$ is a linear $C_1C_{40}$ hydrocarbon radical optionally containing hetexoatonis; $T^1$, $T^2$, $T^3$ and $T^4$ are an oxygen or sulfur atom or a $C(R^{18})_2$ group with the proviso that at least one group between $T^1$ and $T^2$ is an oxygen or a sulfur atom; wherein $R^{18}$, are hydrogen atoms or a $C_1$-$C_{4O}$ hydrocarbon radical; n is 1, 2 or 3; $R^4$ is a hydrogen atom or a $C_1$-$C_{40}$ hydro carbon radical; W is an aromatic 5 or 6 membered ring.

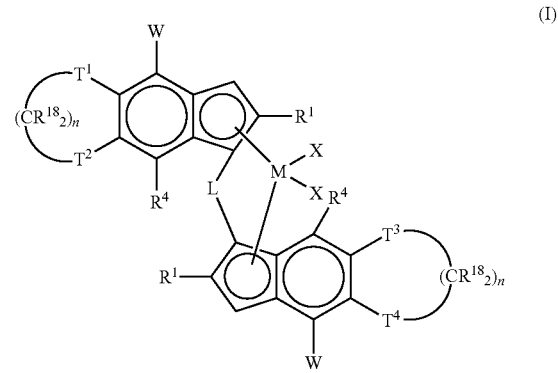

17 Claims, No Drawings

U.S. PATENT DOCUMENTS

| | | |
|---|---|---|
| 6,878,786 B2 | 4/2005 | Resconi et al. |
| 6,949,614 B1 | 9/2005 | Schottek et al. |
| 6,953,829 B2 | 10/2005 | Kratzer et al. |
| 6,963,017 B2 | 11/2005 | Bingel et al. |
| 7,038,070 B2 | 5/2006 | Bingel et al. |
| 7,053,160 B1 | 5/2006 | Bingel et al. |
| 7,101,940 B2 | 9/2006 | Schottek et al. |
| 7,112,638 B2 | 9/2006 | Nifant'ev et al. |
| 7,141,527 B1 | 11/2006 | Van Baar et al. |
| 7,141,637 B2 | 11/2006 | Elder et al. |
| 7,314,903 B2 | 1/2008 | Resconi et al. |
| 7,446,216 B2 * | 11/2008 | Voskoboynikov et al. ..... 556/53 |
| 7,452,949 B2 * | 11/2008 | Okumura et al. ............ 526/160 |
| 2003/0149199 A1 | 8/2003 | Schottek et al. |
| 2004/0132612 A1 | 7/2004 | Resconi et al. |
| 2006/0020096 A1 | 1/2006 | Schottek et al. |
| 2006/0052553 A1 | 3/2006 | Resconi et al. |
| 2006/0235173 A1 | 10/2006 | Resconi |
| 2007/0155919 A1 | 7/2007 | Okumura et al. |
| 2007/0260023 A1 | 11/2007 | Jones et al. |
| 2007/0276095 A1 | 11/2007 | Resconi et al. |

FOREIGN PATENT DOCUMENTS

| | | |
|---|---|---|
| DE | 19962814 | 6/2001 |
| DE | 19962910 | 7/2001 |
| EP | 172961 | 3/1986 |
| EP | 576970 | 1/1994 |
| EP | 633272 | 1/1995 |
| EP | 775707 | 5/1997 |
| EP | 938491 | 9/1999 |
| GB | 1575894 | 10/1980 |
| JP | 4016851 | 1/1992 |
| JP | 4016853 | 1/1992 |
| JP | 4016854 | 1/1992 |
| JP | 4-31868 A * | 2/1992 |
| JP | 4031868 | 2/1992 |
| WO | 91/02012 | 2/1991 |
| WO | 92/00333 | 1/1992 |
| WO | 95/32995 | 12/1995 |
| WO | 98/40331 | 9/1998 |
| WO | 99/21899 | 5/1999 |
| WO | 99/45043 | 9/1999 |
| WO | 00/31090 | 6/2000 |
| WO | 01/21674 | 3/2001 |
| WO | 01/44318 | 6/2001 |
| WO | 01/47939 | 7/2001 |
| WO | 01/48034 | 7/2001 |
| WO | 01/62764 | 8/2001 |
| WO | 02/102811 | 12/2002 |
| WO | 03/045964 | 6/2003 |
| WO | 03/050131 | 6/2003 |
| WO | 2004/005360 | 1/2004 |
| WO | 2004/050724 | 6/2004 |
| WO | 2004/099269 | 11/2004 |
| WO | 2005/023889 | 3/2005 |
| WO | 2005/058916 | 6/2005 |
| WO | WO 2005/058916 A1 * | 6/2005 |
| WO | 2005/095468 | 10/2005 |
| WO | 2005/095473 | 10/2005 |
| WO | 2005/095474 | 10/2005 |
| WO | 2005/118654 | 12/2005 |
| WO | 2006/097497 | 9/2006 |
| WO | 2006/100258 | 9/2006 |
| WO | 2006/100269 | 9/2006 |
| WO | 2006/117285 | 11/2006 |
| WO | 2006/120177 | 11/2006 |

OTHER PUBLICATIONS

M. Kakugo et al., "$^{13}$C NMR Determination of Monomer Sequence Distribution in Ethylene-Propylene Copolymers Prepared with δ-TiCl$_3$-Al(C$_2$H$_5$)$_2$Cl," *Macromolecules*, vol. 15(4), p. 1150-1152 (1982).

A. Rossi et al., "End Groups in 1-Butene Polymerization via Methylaluminoxane and Zirconocene Catalyst," *Macromolecules*, vol. 28(6), p. 1739-1749 (1995).

N. Naga et al., "Effect of co-catalyst system on α-olefin polymerization with *rac-* and *meso-* [dimethylsilylenebis(2,3,5-trimethyl-cyclopentadienyl)]zirconium dichloride," *Macromol. Rapid Commun.*, vol. 18, p. 581-589 (1997).

L. Resconi et al., "$C_1$-Symmetric Heterocyclic Zirconocenes as Catalysts for Propylene Polymerization, 2; *ansa-*Zirconocenes with Linked Dithienocyclopentadienyl-Substituted Indenyl Ligands," *Macromol. Chem. Phys.*, vol. 206, p. 1405-1438 (2005).

C. Cobzaru et al., "Novel High and Ultrahigh Molecular Weight Poly(propylene) Plastomers by Asymmetric Hafnocene Catalysts," *Macromol. Chem. Phys.*, vol. 206, p. 1231-1240 (2005).

L. Resconi et al., "Selectivity in Propene Polymerization with Metallocene Catalysts," *Chem. Rev.*, vol. 100(4), p. 1253-1345 (2000).

* cited by examiner

METALLOCENE COMPOUNDS

The present invention relates to a class of bridged bis indenyl metallocene compounds, wherein the indenyl moieties are, in particular, substituted in position 4 by an aromatic moiety and they are further substituted in positions 5 and 6 by a condensed ring, wherein this ring contains at least one or two oxygen or sulfur atoms. The present invention further relates to the catalyst system thereof and the polymerization process therefrom.

Metallocene compounds are well known in the art as catalyst components for the polymerization of olefins. WO 03/050131 relates to a class of bis indenyl metallocene compounds wherein the indenyl moieties are at least substituted in position 4 and 5. However WO 03/050131 does not report that the substituents on positions 5 and 6 can form a condensed ring. PCT/EP03/12236 relates to a bis indenyl metallocene compound substituted at least in positions 2 5 and 6, wherein the substituents in positions 5 and 6 form a condensed ring. However the substituent in position 4 is defined only in a generic way and in the compounds exemplified in the examples it is always a hydrogen atom. In PCT/EP2004/013827 a class of bis indenyl metallocene compounds wherein the indenyl moieties are substituted in position 5 and 6 by a condensed ring is disclosed. PCT/EP2004/013827 is mainly focused on structures wherein the position 1 of the two indenyl moieties are different, in particular one is branched in alpha position.

All the compounds disclosed in these documents are able to polymerize alpha-olefins, in particular propylene. However there still is the need to find a new class of metallocene compounds able to polymerize olefin in higher yields and to produce polymers having very high molecular weight.

An object of the present invention is a bridged metallocene compound of formula (I)

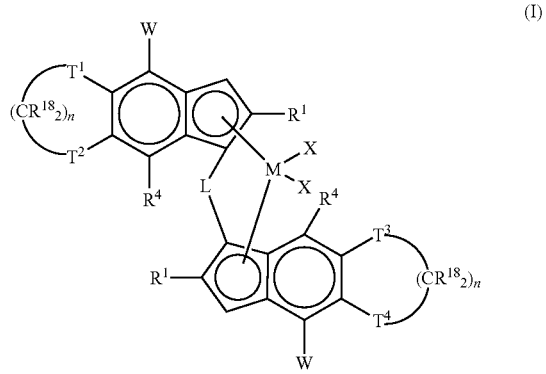

wherein:

M is an atom of a transition metal selected from those belonging to group 3, 4, or to the lanthanide or actinide groups in the Periodic Table of the Elements; preferably M is zirconium, titanium or hafnium;

X equal to or different from each other, is a hydrogen atom, a halogen atom, a R, OR, $OSO_2CF_3$, OCOR, SR, $NR_2$ or $PR_2$ group wherein R is a linear or branched, cyclic or acyclic, $C_1$-$C_{40}$-alkyl, $C_2$-$C_{40}$-alkenyl, $C_2$-$C_{40}$-alkynyl, $C_6$-$C_{40}$-aryl, $C_7$-$C_{40}$-alkylaryl or $C_7$-$C_{40}$-arylalkyl radical; optionally containing heteroatoms belonging to groups 13-17 of the Periodic Table of the Elements; or two X groups can be joined to form a OR'O group wherein R' is a $C_1$-$C_{20}$-alkylidene, $C_6$-$C_{20}$-arylidene, $C_7$-$C_{20}$-alkylarylidene, or $C_7$-$C_{40}$-arylalkylidene radical; preferably X is a hydrogen atom, a halogen atom, a OR'O or R group; more preferably X is chlorine or a methyl radical;

L is a divalent bridging group selected from $C_1$-$C_{20}$ alkylidene, $C_3$-$C_{20}$ cycloalkylidene, $C_6$-$C_{20}$ arylidene, $C_7$-$C_{20}$ alkylarylidene, or a $C_7$-$C_{20}$ arylalkylidene radicals, optionally containing heteroatoms belonging to groups 13-17 of the Periodic Table of the Elements, or it is a silylidene radical containing up to 5 silicon atoms; preferably L is $Si(R^{11})_2$ wherein $R^{11}$ is a linear or branched, cyclic or acyclic, $C_1$-$C_{40}$-alkyl, $C_2$-$C_{40}$ alkenyl, $C_2$-$C_{40}$ alkynyl, $C_6$-$C_{40}$-aryl, $C_7$-$C_{40}$-alkylaryl or $C_7$-$C_{40}$-arylalkyl radical; more preferably L is $Si(CH_3)_2$ or $SiPh_2$;

$R^1$ is a linear $C_1$-$C_{40}$ hydrocarbon radical optionally containing heteroatoms belonging to groups 13-17 of the Periodic Table of the Elements such as methyl or ethyl radical or an alpha branched aryl or arylalkyl radical containing from 2 to 20 carbon atoms optionally containing O, N, S, P and Se atoms, in particular O, N and S atoms such as 2(5-Methiophenyl) or 2(5-Me-furanyl) radicals; preferably $R^1$ is a linear $C_1$-$C_{20}$-alkyl, $C_2$-$C_{40}$ alkenyl, $C_2$-$C_{40}$ alkynyl radical, optionally containing heteroatoms belonging to groups 13-17 of the Periodic Table of the Elements; preferably $R^1$ is a linear $C_1$-$C_{10}$-alkyl radical; more preferably $R^1$ is a methyl, or ethyl radical;

$T^1$ and $T^2$, equal to or different from each other, are an oxygen or sulfur atom or a $C(R^{18})_2$ group, with the proviso that at least one group between $T^1$ and $T^2$ is an oxygen or a sulfur atom; preferably $T^1$ is an oxygen or a sulfur atom, more preferably $T^1$ and $T^2$ are oxygen atoms;

wherein $R^{18}$, equal to or different from each other, are hydrogen atoms or a $C_1$-$C_{40}$ hydrocarbon radical optionally containing one or more heteroatoms belonging to groups 13-17 of the Periodic Table of the Elements; preferably $R^{18}$ is a hydrogen atom or a linear or branched, cyclic or acyclic, $C_1$-$C_{40}$-alkyl, $C_2$-$C_{40}$ alkenyl, $C_2$-$C_{40}$ alkynyl, $C_6$-$C_{40}$-aryl, $C_7$-$C_{40}$-alkylaryl or $C_7$-$C_{40}$-arylalkyl radical, optionally containing one or more heteroatoms belonging to groups 13-17 of the Periodic Table of the Elements; more preferably $R^{18}$ is a hydrogen atom or a linear or branched, $C_1$-$C_{20}$-alkyl radical; more preferably $R^{18}$ is a hydrogen atom or a methyl or ethyl radical;

n is 1, 2 or 3; preferably n is 1 or 2; more preferably n is 1;

$T^3$ and $T^4$, equal to or different from each other, are an oxygen or sulfur atom or a $C(R^{18})_2$ group, wherein $R^{18}$ has been described above $R^4$ is a hydrogen atom or a $C_1$-$C_{40}$ hydrocarbon radical optionally containing heteroatoms belonging to groups 13-17 of the Periodic Table of the Elements; preferably $R^4$ is a hydrogen atom or a linear or branched, cyclic or acyclic, $C_1$-$C_{40}$-alkyl, $C_2$-$C_{40}$ alkenyl, $C_2$-$C_{40}$ alkynyl, $C_6$-$C_{40}$-aryl, $C_7$-$C_{40}$-alkylaryl or $C_7$-$C_{40}$-arylalkyl radical optionally containing heteroatoms belonging to groups 13-17 of the Periodic Table of the Elements; preferably $R^4$ is a hydrogen atom a $C_1$-$C_{10}$-alkyl or a $C_6$-$C_{40}$-aryl radical;

W is an aromatic 5 or 6 membered ring that can contain heteroatoms belonging to groups 15-16 of the Periodic Table of the Elements; the valence of each atom of said ring is substituted with hydrogen atom or it can optionally be substituted with $R^5$ groups, wherein $R^5$, equal to or different from each other, are $C_1$-$C_{40}$ hydrocarbon radicals optionally containing heteroatoms belonging to groups 13-17 of the Periodic Table of the Elements; preferably $R^5$, are linear or branched, cyclic or acyclic, $C_1$-$C_{40}$-alkyl, $C_2$-$C_{40}$ alkenyl, $C_2$-$C_{40}$-alkynyl, $C_6$-$C_{40}$-aryl, $C_7$-$C_{40}$-alkylaryl or $C_7$-$C_{40}$-arylalkyl radicals optionally containing heteroatoms belonging to groups 13-17 of the Periodic Table of the Elements;

Preferably W is selected from the group comprising the following moieties of formula (Wa), (Wb) and (Wc):

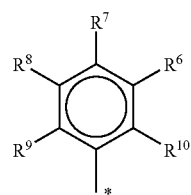
(Wa)

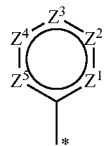
(Wb)

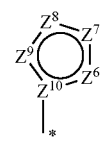
(Wc)

wherein the * represents the point in which the moiety bounds the indenyl moiety of the compound of formula (I);

$R^6$, $R^7$, $R^8$, $R^9$ and $R^{10}$, equal to or different from each other, are hydrogen atoms or $C_1$-$C_{40}$ hydrocarbon radicals optionally containing heteroatoms belonging to groups 13-17 of the Periodic Table of the Elements; preferably $R^6$, $R^7$, $R^8$, $R^9$ and $R^{10}$, are hydrogen atoms or linear or branched, cyclic or acyclic, $C_1$-$C_{40}$-alkyl, $C_2$-$C_{40}$ alkenyl, $C_2$-$C_{40}$ alkynyl, $C_6$-$C_{40}$-aryl, $C_7$-$C_{40}$-alkylaryl or $C_7$-$C_4$-arylalkyl radicals optionally containing heteroatoms belonging to groups 13-17 of the Periodic Table of the Elements;

$Z^1$ is a nitrogen atom or a $CR^{10}$ group; $Z^2$ is a nitrogen atom or a $CR^6$ group; $Z^3$ is a nitrogen atom or a $CR^7$ group; $Z^4$ is a nitrogen atom or a $CR^8$ group; $Z^5$ is a nitrogen atom or a $CR^9$ group; provided that no more than 2 groups among $Z^1$, $Z^2$, $Z^3$, $Z^4$ and $Z^5$ are nitrogen atoms, preferably no more than one group among $Z^1$, $Z^2$, $Z^3$, $Z^4$ and $Z^5$ is a nitrogen atom;

$Z^6$ is an oxygen atom, a sulfur atom, a $NR^{13}$ group or a $CR^{13}$ group; $Z^7$ is an oxygen atom, a sulfur atom, a $NR^{14}$ group or a $CR^{14}$ group; $Z^8$ is an oxygen atom, a sulfur atom, a $NR^{15}$ group or a $CR^{15}$ group; $Z^9$ is an oxygen atom, a sulfur atom, a $NR^{16}$ group or a $CR^{16}$ group;

$Z^{10}$ is a nitrogen atom or a carbon atom that bonds the indenyl moiety of the structure of formula (I); with the proviso that not more than 1 group among $Z^6$, $Z^7$, $Z^8$, $Z^9$ or $Z^{10}$ is a sulfur atom, an oxygen atom or a nitrogen-containing group atom selected from $NR^{13}$, $NR^{14}$, $NR^{15}$, $NR^{16}$, and a nitrogen atom;

$R^{13}$, $R^{14}$, $R^{15}$ and $R^{16}$, equal to or different from each other, are hydrogen atoms or $C_1$-$C_{40}$ hydrocarbon radicals optionally containing heteroatoms belonging to groups 13-17 of the Periodic Table of the Elements; preferably $R^{13}$, $R^{14}$, $R^{15}$ and $R^{16}$, are hydrogen atoms or linear or branched, cyclic or acyclic, $C_1$-$C_{40}$-alkyl, $C_2$-$C_{40}$ alkenyl, $C_2$-$C_{40}$ alkynyl, $C_6$-$C_{40}$-aryl, $C_7$-$C_{40}$-alkylaryl or $C_7$-$C_{40}$-arylalkyl radicals optionally containing heteroatoms belonging to groups 13-17 of the Periodic Table of the Elements; more preferably $R^{13}$, $R^{14}$, $R^{15}$ and $R^{16}$ are hydrogen atoms, $C_1$-$C_{40}$-alkyl or $C_6$-$C_{40}$-aryl radicals;

In the moiety of formula (Wa), in a preferred embodiment, $R^7$ is a $C_1$-$C_{40}$-alkyl radical, preferably a branched $C_1$-$C_{40}$-alkyl radical, more preferably $R^7$ is a branched $C_1$-$C_{40}$-alkyl radical wherein the carbon atom in position alpha is a tertiary carbon atom such as a tertbutyl radical, and $R^6$, $R^8$, $R^9$ and $R^{10}$ are hydrogen atoms;

In a further preferred embodiment $R^{10}$ and $R^8$ are $C_1$-$C_{40}$-alkyl radicals, preferably they are linear $C_1$-$C_{40}$-alkyl radicals such as methyl radicals and $R^7$, $R^8$ and $R^9$ are hydrogen radicals:

In a further preferred embodiment $R^6$, $R^7$ and $R^8$ are linear or branched $C_1$-$C_{40}$-alkyl radicals such as methyl or tertbutyl radicals and $R^{10}$ and $R^9$ are hydrogen atoms.

In a further preferred embodiment $R^6$, $R^7$, $R^8$, $R^9$ and $R^{10}$ are hydrogen atoms;

In the moiety of formula (Wb), in a preferred embodiment, $Z^1$ is a nitrogen atom and $Z^2$, $Z^3$, $Z^4$ and $Z^5$ are respectively $CR^6$, $CR^7$, $CR^8$ and $CR^9$ wherein the meaning of $R^6$, $R^7$, $R^8$, and $R^9$ is described above; in a further preferred embodiment $Z^3$ is a nitrogen atom and $Z^1$, $Z^2$, $Z^4$ and $Z^5$ are respectively $CR^{10}$, $CR^6$, $CR^8$ and $CR^9$ wherein the meaning of $R^{10}$, $R^6$, $R^8$, and $R^9$ is described above; in a further preferred embodiment $Z^2$ is a nitrogen atom and $Z^1$, $Z^3$, $Z^4$ and $Z^5$ are respectively $CR^{10}$, $CR^7$, $CR^8$ and $CR^9$ wherein the meaning of $R^{10}$, $R^7$, $R^8$, and $R^9$ is described above;

In the moiety of formula (Wc) in a preferred embodiment $Z^6$ is an oxygen atom, a sulfur atom, a $NR^{16}$ group; preferably it is a sulfur atom or a $NR^{16}$; wherein $R^{16}$ is preferably a $C_1$-$C_{40}$-alkyl radical; more preferably $Z^6$ is a sulfur atom; and $Z^7$, $Z^8$, $Z^9$ and $Z^{10}$ are respectively a $CR^{14}$, $CR^{15}$, $CR^{16}$ and a carbon atom, wherein $R^{14}$ is a hydrogen atom or a $C_1$-$C_{40}$-alkyl radical such as methyl or ethyl; and $R^{15}$ and $R^{16}$ are hydrogen atoms or $C_1$-$C_{40}$-alkyl radicals.

A preferred subclass of the compounds of formula (I) is represented by compound having formula (Ia)

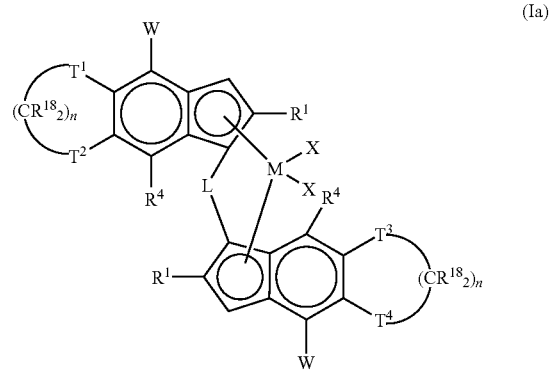
(Ia)

wherein $T^1$, $T^2$, $T^3$ and $T^4$ are oxygen or sulfur atoms, preferably they are oxygen atoms;

n is 1 or 2; preferably n is 1;

M, L, X, W, $R^1$, $R^4$ and $R^{18}$ have the above described meaning.

A further preferred subclass of the compounds of formula (I) is represented by compound having formula (Ib)

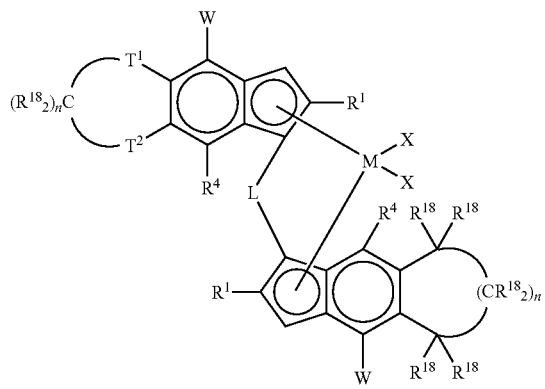

(Ib)

wherein n is 1 or 2; preferably n is 1;

M, L, X, W, $T^1$, $T^2$, $R^1$, $R^4$ and $R^{18}$ have the above described meaning;

A Further preferred class of the compounds of formula (I) is represented by formula (IIa):

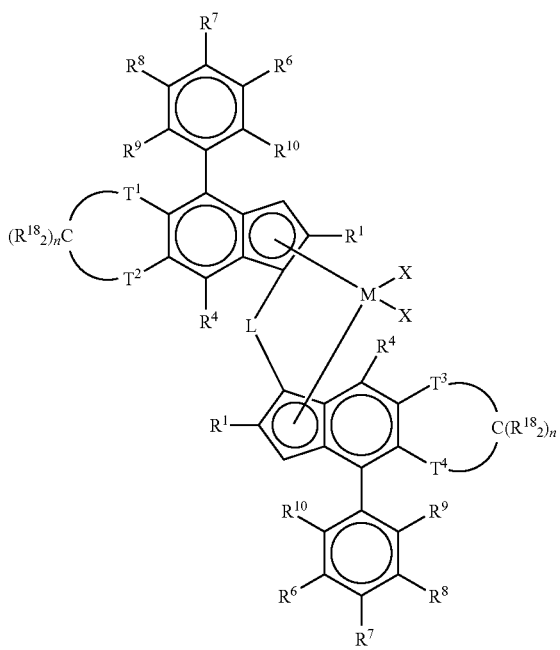

(IIa)

Wherein M, L, X, $T^1$, $T^2$, $T^3$, $R^1$, $R^4$, $R^6$, $R^7$, $R^8$, $R^9$ and $R^{10}$ have the meaning reported above.

A further preferred class of compounds of formula (I) has formula (IIb)

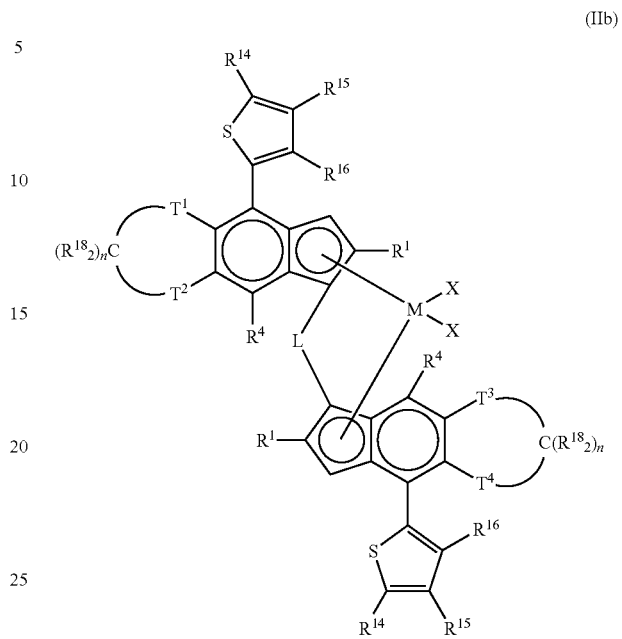

(IIb)

Wherein M, L, X, $T^1$, $T^2$, $T^3$, $T^4$, $R^1$, $R^4$, $R^{14}$, $R^{15}$, $R^{16}$ have the meaning reported above.

Examples of compounds having formula (I) are as follows

Me$_2$Si{8-(4-tBuPh)-6-Me-5H-indeno[5,6-d][1,3]dioxol-5-yl}$_2$ZrC$_2$

Me$_2$Si{6-Me-8-Ph-5H-indeno[5,6-d][1,3]dioxol-5-yl}$_2$ZrCl$_2$

Me$_2$Si{6-Me-8-(2,5-Me$_2$Ph)-5H-indeno[5,6-d][1,3]dioxol-5-yl}$_2$ZrCl$_2$

Me$_2$Si(3,5-dihydro-6-Me-8-Ph-2H-indeno[5,6-b]furan-5-yl)$_2$ZrC$_2$

Me$_2$Si(2,3,4,6-tetrahydro-7-Me-9-Ph-cyclopenta[g]chromen-6-yl)$_2$ZrC$_2$

Me$_2$Si(6-Me-8-(2,5-Me$_2$Ph)-5H-indeno[5,6-d][1,3]dithiol-5-yl)$_2$ZrCl$_2$

Me$_2$Si(6-Me-8-Ph-5H-indeno[5,6-d][1,3]dithiol-5-yl)$_2$ZrC$_2$

Me$_2$Si{8-(4-tBuPh)-6-Me-5H-indeno[5,6-d][1,3]dithiol-5-yl}$_2$ZrCl$_2$

Me$_2$Si(2,3,4,6-tetrahydro-7-Me-9-Ph-cyclopenta[g]thiochromen-6-yl)$_2$ZrC$_2$

Me$_2$Si{6-Me-8-(2,5-Me$_2$-pyrrol-1-yl)-5H-indeno[5,6-d][1,3]dioxol-5-yl}$_2$ZrCl$_2$ Me$_2$Si{6-Me-8-(2,3-Me$_2$-indol-1-yl)-5H-indeno[5,6-d][1,3]dioxol-5-yl}$_2$ZrCl$_2$ Me$_2$Si{6-Me-8-(pyridin-4-yl)-5H-indeno[5,6-d][1,3]dioxol-5-yl}$_2$ZrC$_2$ and their correspondent dimethyl derivatives and further the corresponding titanium, and hafnium compounds.

Preferably the metallocene compounds object of the present invention are in their racemic(rac) or racemic like form.

For the purpose of the present invention the term "racemic (rac) form" means that the same substituents on the two cyclopentadienyl moieties are on the opposite side with respect to the plane containing the zirconium and the centre of the said cyclopentadienyl moieties. "racemic-like form" means that the bulkier substituents of the two cyclopentadienyl moieties on the metallocene compound are on the opposite side with respect to the plane containing the zirconium and the centre of the said cyclopentadienyl moieties as shown in the following compound:

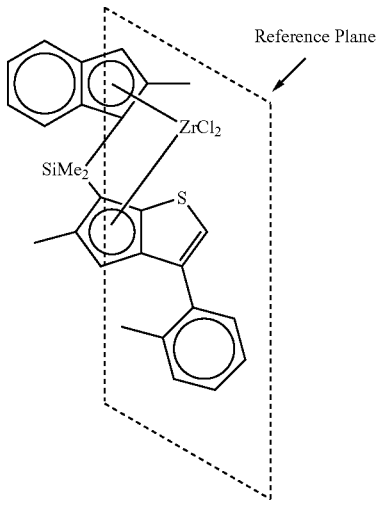

A further object of the present invention is a catalyst system for the polymerization of olefin obtainable by contacting:

a) a metallocene compound of formula (I);

b) at least an alumoxane or a compound able to form an alkylmetallocene cation; and c) optionally an organo aluminum compound.

Preferably the metallocene compounds have formulas selected from (Ia), (Ib), (Ic), (IIa) or (IIb). Alumoxanes used as component b) in the catalyst system according to the present invention can be obtained by reacting water with an organo-aluminium compound of formula $H_jAlU_{3-j}$ or $H_jAl_2U_{6-j}$, where the U substituents, same or different, are hydrogen atoms, halogen atoms, $C_1$-$C_{20}$-alkyl, $C_3$-$C_{20}$-cyclalkyl, $C_6$-$C_{20}$-aryl, $C_7$-$C_{20}$-alkylaryl or $C_7$-$C_{20}$-arylalkyl radicals, optionally containing silicon or germanium atoms, with the proviso that at least one U is different from halogen, and j ranges from 0 to 1, being also a non-integer number. In this reaction the molar ratio of Al/water is preferably comprised between 1:1 and 100:1.

The alumoxanes used in the catalyst system according to the invention are considered to be linear, branched or cyclic compounds containing at least one group of the type:

wherein the substituents U, same or different, are defined above.

In particular, alumoxanes of the formula:

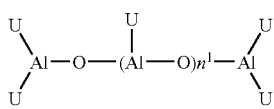

can be used in the case of linear compounds, wherein $n^1$ is 0 or an integer of from 1 to 40 and the substituents U are defined as above; or alumoxanes of the formula:

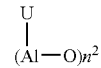

can be used in the case of cyclic compounds, wherein $n^2$ is an integer from 2 to 40 and the U substituents are defined as above.

Examples of alumoxanes suitable for use according to the present invention are methylalumoxane (MAO), tetra-(isobutyl)alumoxane (TIBAO), tetra-(2,4,4-trimethyl-pentyl)alumoxane (TIOAO), tetra-(2,3-dimethylbutyl)alumoxane (TDMBAO) and tetra-(2,3,3-trimethylbutyl)alumoxane (TTMBAO).

Particularly interesting cocatalysts are those described in WO 99/21899 and in WO01/21674 in which the alkyl and aryl groups have specific branched patterns.

Non-limiting examples of aluminium compounds that can be reacted with water to give suitable alumoxanes (b), described in WO 99/21899 and WO01/21674, are:

tris(2,3,3-trimethyl-butyl)aluminium, tris(2,3-dimethyl-hexyl)aluminium, tris(2,3-dimethyl-butyl)aluminium, tris(2,3-dimethyl-pentyl)aluminium, tris(2,3-dimethyl-heptyl)aluminium, tris(2-methyl-3-ethyl-pentyl)aluminium, tris(2-methyl-3-ethyl-hexyl)aluminium, tris(2-methyl-3-ethyl-heptyl)aluminium, tris(2-methyl-3-propyl-hexyl)aluminium, tris(2-ethyl-3-methyl-butyl)aluminium, tris(2-ethyl-3-methyl-pentyl)aluminium, tris(2,3-diethyl-pentyl)aluminium, tris(2-propyl-3-methyl-butyl)aluminium, tris(2-isopropyl-3-methyl-butyl)aluminium, tris(2-isobutyl-3-methyl-pentyl)aluminium, tris(2,3,3-trimethyl-pentyl)aluminium, tris(2,3,3-trimethyl-hexyl)aluminium, tris(2-ethyl-3,3-dimethyl-butyl)aluminium, tris(2-ethyl-3,3-dimethyl-pentyl)aluminium, tris(2-isopropyl-3,3-dimethyl-butyl)aluminium, tris(2-trimethylsilyl-propyl)aluminium, tris(2-methyl-3-phenyl-butyl)aluminium, tris(2-ethyl-3-phenyl-butyl)aluminium, tris(2,3-dimethyl-3-phenyl-butyl)aluminium, tris(2-phenyl-propyl)aluminium, tris[2-(4-fluorophenyl)-propyl]aluminium, tris[2-(4-chloro-phenyl)-propyl] aluminium, tris[2-(3-isopropyl-phenyl)-propyl]aluminium, tris(2-phenyl-butyl)aluminium, tris(3-methyl-2-phenyl-butyl)aluminium, tris(2-phenyl-pentyl)aluminium, tris[2-(pentafluorophenyl)-propyl]aluminium, tris[2,2-diphenyl-ethyl] aluminium and tris[2-phenyl-2-methyl-propyl]aluminium, as well as the corresponding compounds wherein one of the hydrocarbyl groups is replaced with a hydrogen atom, and those wherein one or two of the hydrocarbyl groups are replaced with an isobutyl group.

Amongst the above aluminium compounds, trimethylaluminium (TMA), triisobutylaluminium (TIBA), tris(2,4,4-trimethyl-pentyl)aluminium (TIOA), tris(2,3-dimethylbutyl) aluminium (TDMBA) and tris(2,3,3-trimethylbutyl) aluminium (TTMBA) are preferred Non-limiting examples of compounds able to form an alkylmetallocene cation are compounds of formula $D^+E^-$, wherein $D^+$ is a Brønsted acid, able to donate a proton and to react irreversibly with a substituent X of the metallocene of formula (I) and $E^-$ is a compatible anion, which is able to stabilize the active catalytic species originating from the reaction of the two compounds, and which is sufficiently labile to be removed by an olefinic monomer. Preferably, the anion $E^-$ comprises one or more boron atoms. More preferably, the anion E⁻ is an anion of the formula $BAr_{41}^{(-)}$, wherein the substituents Ar which can be identical or different are aryl radicals such as phenyl, pentafluorophenyl or bis(trifluoromethyl)phenyl. Tetrakis-pentafluorophenyl borate is particularly preferred compound, as described in WO 91/02012. Moreover, compounds of formula $BAr_3$ can be conveniently used. Compounds of this type are described, for example, in the International patent application WO 92/00333. Other examples of compounds able to form an alkylmetallocene cation are compounds of formula $BAr_3P$ wherein P is a substituted or unsubstituted pyrrol radical. These compounds are described in WO01/62764. Compounds containing boron atoms can be conveniently supported according to the description of DE-A-19962814 and DE-A-19962910. All these compounds containing boron atoms can be used in a molar ratio between boron and the metal of the metallocene comprised between about 1:1 and about 10:1; preferably 1:1 and 2.1; more preferably about 1:1.

Non limiting examples of compounds of formula D⁺E⁻ are:
Tributylammoniumtetra(pentafluorophenyl)borate,
Tributylammoniumtetra(pentafluorophenyl)aluminate,
Tributylammoniumtetra(trifluoromethylphenyl)borate,
Tributylammoniumtetra(4-fluorophenyl)borate,
N,N-Dimethylbenzylammonium-tetralispentafluorophenylborate,
N,N-Dimethylhexylamonium-tetrakispentafluorophenylborate,
N,N-Dimethylaniliniumtetrakis(pentafluorophenyl)borate,
N,N-Dimethylaniliniumtetrs(pentafluorophenyl)aluminate,
N,N-Dimethylbenzylammonium-tetrakispentafluorophenylborate,
N,N-Dimethylhexylamonium-tetrakispentafluorophenylborate,
Di(propyl)ammoniumtetrakis(pentafluorophenyl)borate,
Di(cyclohexyl)ammoniumtetrakis(pentafluorophenyl)borate,
Triphenylcarbeniumtetrakis(pentafluorophenyl)borate,
Triphenylcarbeniumtetrakis(pentafluorophenyl)aluminate,
Ferroceniumtetrakis(pentafluorophenyl)borate,
Ferroceniumtetrakis(pentafluorophenyl)aluminate.
Triphenylcarbeniumtetrais(pentafluorophenyl)borate, and
N,N-Dimethylaniliniumtetrakis(pentafluorophenyl)borate.

Organic aluminum compounds used as compound c) are those of formula $H_jAlU_{3-j}$ or $H_jAl_2U_{6-j}$ as described above.

The catalysts of the present invention can also be supported on an inert carrier. This is achieved by depositing the metallocene compound a) or the product of the reaction thereof with the component b), or the component b) and then the metallocene compound a) on an inert support. The support can be a porous solid such as talc, a sheet silicate, an inorganic oxide or a finely divided polymer powder (e.g. polyolefin). Suitable inorganic oxides may be found among the oxides of elements of groups 2, 3, 4, 5, 13, 14, 15 and 16 of the Periodic Table of the Elements. Examples of oxides preferred as supports include silicon dioxide, aluminum oxide, and also mixed oxides of the elements calcium, aluminum, silicon, magnesium or titanium and also corresponding oxide mixtures, magnesium halides, styrene/divinylbenzene copolymers, polyethylene or polypropylene. Other inorganic oxides which can be used alone or in combination with the abovementioned preferred oxidic supports are, for example, MgO, $ZrO_2$, $TiO_2$ or $B_2O_3$.

A suitable class of supports which can be used is that constituted by porous organic supports functionalized with groups having active hydrogen atoms. Particularly suitable are those in which the organic support is a partially crosslinked styrene polymer. Supports of this type are described in European application EP-633 272.

Another class of inert supports particularly suitable for use according to the invention is that of polyolefin porous prepolymers, particularly polyethylene.

A further suitable class of inert supports for use according to the invention is that of porous magnesium halides such as those described in International application WO 95/32995.

The support materials used preferably have a specific surface area in the range from 10 to 1 000 m²/g, a pore volume in the range from 0.1 to 5 ml/g and a mean particle size of from 1 to 500 µm. Preference is given to supports having a specific surface area in the range from 50 to 500 m²/g, a pore volume in the range from 0.5 to 3.5 ml/g and a mean particle size in the range from 5 to 350 µm. Particular preference is given to supports having a specific surface area in the range from 200 to 400 m²/g, a pore volume in the range from 0.8 to 3.0 ml/g and a mean particle size of from 10 to 300 µm.

The inorganic support can be subjected to a thermal treatment, e.g. to remove adsorbed water. Such a drying treatment is generally carried out at from 80 to 300° C., preferably from 100 to 200° C., with drying at from 100 to 200° C. preferably being carried out under reduced pressure and/or a blanket of inert gas (e.g. nitrogen), or the inorganic support can be calcined at from 200 to 1000° C. to produce the desired structure of the solid and/or set the desired OH concentration on the surface. The support can also be treated chemically using customary desiccants such as metal alkyls, preferably aluminum alkyls, chlorosilanes or $SiCl_4$, or else methylaluminoxane. Appropriate treatment methods are described, for example, in WO 00/31090.

The inorganic support material can also be chemically modified. For example, treatment of silica gel with $(NH_4)_2SiF_6$ leads to fluorination of the silica gel surface, or treatment of silica gels with silanes containing nitrogen-, fluorine- or sulfur-containing groups leads to correspondingly modified silica gel surfaces.

Organic support materials such as finely divided polyolefin powders (e.g. polyethylene, polypropylene or polystyrene) can also be used and are preferably likewise freed of adhering moisture, solvent residues or other impurities by means of appropriate purification and drying operations before use. It is also possible to use functionalized polymer supports, e.g. supports based on polystyrene, via whose functional groups, for example ammonium or hydroxy groups, at least one of the catalyst components can be immobilized. The solid compound obtained by supporting the catalyst system object of the present invention on a carrier in combination with the further addition of the alkylaluminium compound either as such or prereacted with water if necessary, can be usefully employed in the gas-phase or slurry polymerization.

The catalyst system of the present invention can be used also in a solution polymerization process. For the purpose of the present invention the term solution polymerization means preferably that the polymer is fully soluble in the polymerization medium at the polymerization temperature used, and in a concentration range of at least 5% by weight; more preferably from 5 to 50% by weight.

In order to have the polymer completely soluble in the polymerization medium, a mixtures of monomers for copolymers or only one monomer for homopolymers in the presence of an inert solvent can be used. This solvent can be an aliphatic or cycloaliphatic hydrocarbon such as butane, hexane, heptane isooctane, cyclohexane and methylcyclohexane. It is also possible to use mineral spirit or a hydrogenated diesel oil fraction. Also aromatic hydrocarbons can be used such as toluene. Preferred solvents to be used are cyclohexane and methylcyclohexane. In case propylene is used as monomer for the obtainment of propylene copolymers in solution polymerization process, the propylene content in the liquid phase of the polymerization medium preferably ranges from 5% to 60% by weight; more preferably from 20% to 50% by weight.

The catalyst system comprising the metallocene compound of formula (I) can be used for polymerizing olefins, in particular alpha-olefins in high yields to obtain polymers having high molecular weight. Therefore a further object of the present invention is a process for preparing a alpha-olefin polymer comprising contacting under polymerization conditions one or more alpha-olefins of formula $CH_2$=CHA wherein A is hydrogen or a $C_1$-$C_{20}$ alkyl radical, in the presence of a catalyst system as described above.

Non limitative examples of alpha-olefins of formula $CH_2$=CHA are: ethylene, propylene, 1-butene, 1-hexene, 1-octene and 4-methyl-1-pentene, preferred alpha olefins are ethylene, propylene and 1-butene.

The metallocene compounds of formula (I) object of the present invention are particularly suitable for the homo and copolymerization of propylene. In fact, the metallocene-based catalyst system of the present invention when used for homo or copolymerizing propylene are able to give polymers having a high molecular weight in high yields also at high temperatures rendering thus possible to use it in the industrial plants that use polymerization temperatures higher than 50° C. and that can be comprised between 60° and 200° C., preferably between 60° C. and 120° C. As said above, the metallocene compounds of formula (I) are particularly suitable for the copolymerization of propylene, therefore a further object of the present invention is a process for the preparation of propylene copolymers comprising the step of contacting, under polymerization conditions, propylene with ethylene or one or more alpha olefins of formula $CH_2$=$CHA^1$, wherein $A^1$ is a $C_2$-$C_{20}$ alkyl radical, in the presence of a catalyst system described above. This process is preferably carried out in solution as described above.

Examples of alpha olefins of formula $CH_2$=$CHA^1$ are ethylene, 1-butene, 1-hexene, 1-octene and 4-methyl-1-pentene, preferred alpha olefins are ethylene and 1-butene; more preferred alpha olefin is ethylene.

The content of alpha-olefins derived units in the propylene copolymer object of the present invention ranges from 0.1 to 90% by mol; preferably it ranges from 5% by mol to 70% by mol; more preferably it ranges from 10% by mol to 60% by mol.

The metallocene compounds of the present invention are also particularly suitable for the preparation of copolymers of ethylene and higher alpha olefins, such as propylene, 1-butene, 1-hexene, 1-octene. The copolymers have a comonomer content ranging from 5 to 50% by mol. Particularly preferred are ethylene/1-butene copolymer having a content of 1-butene derive units ranging from 5 to 50% by mol. Said copolymers can be obtained in high yields by using a gas phase process such a fluidized bed or stirred bed reactor.

As explained above the process for the polymerization of olefins according to the invention can be carried out in the liquid phase in the presence or absence of an inert hydrocarbon solvent, such as in in slurry, or in the gas phase. The hydrocarbon solvent can either be aromatic such as toluene, or aliphatic such as propane, hexane, heptane, isobutane or cyclohexane.

As a general rule, the polymerization temperature is generally comprised between −100° C. and +200° C. and, particularly between 10° C. and +100° C. The polymerization pressure is generally comprised between 0.5 and 100 bar.

The lower the polymerization temperature, the higher are the resulting molecular weights of the polymers obtained.

The polymerization yields depend on the purity of the metallocene compound of the catalyst The metallocene compounds obtained by the process of the invention can therefore be used as such or can be subjected to purification treatments.

In view of the optimum behavior of the metallocene compounds of formula (I) when used for the homo and copolymerization of propylene, the catalyst system based on the metallocene compounds object of the present invention can be used in a multistage process for preparing heterophasic propylene copolymers. Therefore a further object of the present invention is a multistage polymerization process comprising the following steps:

a) polymerizing propylene with optionally ethylene or one or more alpha olefins of formula $CH_2$=$CHA^1$, wherein $A^1$ is a $C_2$-$C_{20}$ alkyl radical, in the presence of a catalysts system described above;

b) contacting, under polymerization conditions, propylene with ethylene or one or more alpha olefins of formula $CH_2$=$CHA^1$, and optionally with a non-conjugated diene, in the presence of the polymer obtained in step a) and optionally in the presence of an additional organo aluminum compound;

provided that the polymer produced in step a) is different from the copolymer produced in step b) for the comonomer derived units amount or comonomer derived units structure;

wherein the amount of the polymer obtained in step a) ranges from 2% to 98% by weight of the polymer obtained in the whole process and the amount of polymer obtained in step b) ranges from 98% to 2% by weight of the polymer obtained in the whole process.

Preferably step a) further comprises a prepolymerization step a-1).

The prepolymerization step a-1) can be carried out by contacting the catalyst system described above with one or more alpha olefins of formula $CH^2$=CHA wherein A is hydrogen or a $C_1$-$C_{20}$ alkyl radical; preferably said alpha olefin is propylene or ethylene, at a temperature ranging from −20° C. to 70° C., in order to obtain a prepolymerized catalyst system containing preferably from 5 to 500 g of polymer per gram of catalyst system.

Step a) of the present invention can be carried out in liquid phase, in which the polymerization medium can be an inert hydrocarbon solvent or the polymerization medium can be liquid propylene optionally in the presence of an inert hydrocarbon solvent, and of ethylene or one or more comonomer of formula $CH_2$=$CHA^1$, or step a) can be carried out in a gas phase. Said hydrocarbon solvent can be either aromatic (such as toluene) or aliphatic (such as propane, hexane, heptane, isobutane, cyclohexane and 2,2,4-trimethylpentane).

Preferably the polymerization medium is liquid propylene. It can optionally contains minor amounts (up to 20% by weight, preferably up to 10% by weight, more preferably up to 5% by weight) of an inert hydrocarbon solvent or of ethylene or one or more comonomer of formula $CH_2$=$CHA^1$.

Step a) can be carried out in the presence of hydrogen. The amount of hydrogen present during the polymerization reaction is preferably more than 1 ppm; more preferably from 5 to 2000 ppm; even more preferably from 6 to 500 ppm with respect to the propylene present in the reactor. Hydrogen can be added either at the beginning of the polymerization reaction or it can also be added at a later stage after a prepolymerization step has been carried out.

The propylene polymer obtained in step a) is a propylene homopolymer or a propylene copolymer containing up to 20% by mol preferably from 0.1 to 10% by mol, more preferably from 1% to 5% by mol of derived units of ethylene or one or more alpha olefins of formula $CH_2\!=\!CHA^1$. Preferred comonomers are ethylene or 1-butene. Preferably in step a) a propylene homopolymer is produced.

The content of the polymer obtained in step a) preferably ranges from 5% to 90% by weight of the polymer produced in the whole process, more preferably it ranges from 10% to 70% by weight and still more preferably from 25% to 65% by weight of the total polymer produced in the whole process.

Step b) can be carried out in liquid phase, in which the polymerization medium can be an inert hydrocarbon solvent or the polymerization medium can be liquid propylene optionally in the presence of an inert hydrocarbon solvent, and of ethylene or one or more comonomer of formula $CH_2\!=\!CHA^1$, or step a) can be carried out in a gas phase. Preferably step b) is carried out in a gas phase, preferably in a fluidized or stirred bed reactor. The polymerization temperature is generally comprised between −100° C. and +200° C., and, preferably, between 10° C. and +90° C. The polymerization pressure is generally comprised between 0.5 and 100 bar.

In step b) a propylene copolymer containing from 5% to 90% by mol, preferably from 10% to 50% by mol, more preferably from 15% to 30% by mol of derived units of ethylene or one or more alpha olefins of formula $CH_2\!=\!CHA^1$ is produced. Examples of comonomer of formula $CH_2\!=\!CHA^1$ that can be used in step b) of the present invention are: 1-butene, 1-pentene, 4-methyl-1-pentene, 1-hexene, 1-octene, 4,6-dimethyl-1-heptene, 1-decene, 1-dodecene, 1-tetradecene, 1-hexadecene, 1-octadecene and 1-eicosene. Preferred comonomers are ethylene or 1-butene.

The content of polymer obtained in step b) preferably ranges from 10 to 95% by weight of the polymer produced in the whole process, preferably it ranges from 30% to 90% by weight and more preferably from 35% to 75% by weight.

The polymer obtained in step b) can optionally contains up to 20% by mol of a non conjugated diene. Non conjugated dienes can be a straight chain, branched chain or cyclic hydrocarbon diene having from 6 to 20 carbon atoms. Examples of suitable non-conjugated dienes are:

straight chain acyclic dienes, such as 1,4-hexadiene and 1,6-octadiene;

branched chain acyclic dienes, such as 5-methyl-1,4-hexadiene, 3,7-dimethyl-1,6-octadiene, 3,7-dimethyl-1,7-octadiene and mixed isomers of dihydro myricene and dihydroocinene;

single ring alicyclic dienes, such as 1,3-cyclopentadiene, 1,4-cyclohexadiene, 1,5-cyclooctadiene and 1,5-cyclododecadiene;

multi-ring alicyclic fused and bridged ring dienes, such as tetrahydroindene, methyl tetrahydroindene, dicyclopentadiene, bicyclo-(2,2,1)-hepta-2,5-diene; and alkenyl, alkylidene, cycloalkenyl and cycloalkylidene norbornenes, such as 5-methylene-2-norbornene (MNB), 5-propenyl-2-norbornene, 5-isopropylidene-2-norbornene, 5-(4-cyclopentenyl)-2-norbornene, 5-cyclohexylidene-2-norbornene, 5-vinyl-2-norbornene and norbornadiene.

Preferred dienes are 1,4-hexadiene (HD), 5-ethylidene-2-norbornene (ENB), 5-vinylidene-2-norbornene (VNB), 5-methylene-2-norbornene (MNB) and dicyclopentadiene (DCPD). Particularly preferred dienes are 5-ethylidene-2-norbornene (ENB) and 1,4-hexadiene (HD).

When present the non-conjugated dienes are preferably incorporated into the polymer in an amount from 0.1% to about 20% by mol, preferably from 0.5% to 15% by mol, and more preferably from 0.5% to 7% by mol. If desired, more than one diene may be incorporated simultaneously, for example HD and ENB, with total diene incorporation within the limits specified above.

A further multistage polymerization process process comprises the following steps:

a1) polymerizing propylene with optionally ethylene or one or more monomers selected from alpha olefins of formula $CH_2\!=\!CHA^1$, wherein $A^1$ is a $C_2$-$C_{20}$ alkyl radical, in the presence of a catalysts system described above;

b1) contacting, under polymerization conditions, ethylene with propylene or one or more alpha olefins of formula $CH_2\!=\!CHA^1$, and optionally with a non-conjugated diene, in the presence of the polymer obtained in step a) and optionally in the presence of an additional organo aluminum compound;

provided that the polymer produced in step a1) is different from the copolymer produced in step b1) for the comonomer derived units amount or comonomer derived units structure;

wherein the amount of the polymer obtained in step a1) ranges from 2% to 98% by weight of the polymer obtained in the whole process and the amount of polymer obtained in step b1) is ranges from 98% to 2% by weight of the polymer obtained in the whole process.

Preferably step a1) further comprises a prepolymerization step a1-1).

The prepolymerization step a1-1) can be carried out by contacting the catalyst system described above with one or more alpha olefins of formula $CH^2\!=\!CHA$ wherein A is hydrogen or a $C_1$-$C_{20}$ alkyl radical; preferably said alpha olefin is propylene or ethylene, at a temperature ranging from 20° C. to 70° C., in order to obtain a prepolymerized catalyst system containing preferably from 5 to 500 g of polymer per gram of catalyst system.

Step a1) can be carried out in liquid phase, in which the polymerization medium can be an inert hydrocarbon solvent or the polymerization medium can be liquid propylene optionally in the presence of an inert hydrocarbon solvent and ethylene or one or more comonomer of formula $CH_2\!=\!CHA^1$, or step a1) can be carried out in a gas phase. Said hydrocarbon solvent can be either aromatic (such as toluene) or aliphatic (such as propane, hexane, heptane, isobutane, cyclohexane and 2,2,4-trimethylpentane).

Preferably the polymerization medium is liquid propylene. It can optionally contains minor amounts (up to 20% by weight, preferably up to 10% by weight, more preferably up to 5% by weight) of an inert hydrocarbon solvent or of ethylene or one or more comonomer of formula $CH_2\!=\!CHA^1$.

Step a1) can be carried out in the presence of hydrogen. The amount of hydrogen present during the polymerization reaction is preferably more than 1 ppm; more preferably from 5 to 2000 ppm; even more preferably from 6 to 500 ppm with respect to the propylene present in the reactor. Hydrogen can be added either at the beginning of the polymerization reaction or it can also be added at a later stage after a prepolymerization step has been carried out.

The propylene polymer obtained in step a1) is a propylene homopolymer or a propylene copolymer containing up to 20% by mol preferably from 0.1 to 10% by mol, more preferably from 1% to 5% by mol of derived units of ethylene or one or more alpha olefins of formula $CH_2\!=\!CHA^1$. Preferred comonomers are ethylene or 1-butene. Preferably in step a 1) a propylene homopolymer is produced.

The content of the polymer obtained in step a1) preferably ranges from 5% to 90% by weight of the polymer produced in the whole process, more preferably it ranges from 10% to 70% by weight and still more preferably from 25% to 65% by weight of the total polymer produced in the whole process.

Step b1) can be carried out in liquid phase, in which the polymerization medium can be an inert hydrocarbon solvent or the polymerization medium can be a liquid monomer such as ethylene, propylene or one or more comonomer of formula $CH_2=CHA^1$ optionally in the presence of an inert hydrocarbon solvent, or step b1) can be carried out in a gas phase. Preferably step b1) is carried out in a gas phase, preferably in a fluidized or stirred bed reactor. The polymerization temperature is generally comprised between $-100°$ C. and $+200°$ C., and, preferably, between $10°$ C. and $+90°$ C. The polymerization pressure is generally comprised between 0.5 and 100 bar.

In step b1) an ethylene copolymer containing from 5% to 90% by mol, preferably from 10% to 50% by mol, more preferably from 15% to 30% by mol of derived units of propylene or one or more alpha olefins of formula $CH_2=CHA^1$ is produced. Examples of comonomer of formula $CH_2=CHA^1$ that can be used in step b1) of the present invention are: 1-butene, 1-pentene, 4-methyl-1-pentene, 1-hexene, 1-octene, 4,6-dimethyl-1-heptene, 1-decene, 1-dodecene, 1-tetradecene, 1-hexadecene, 1-octadecene and 1-eicosene. Preferred comonomers are propylene or 1-butene.

The content of polymer obtained in step b1) preferably ranges from 10 to 95% by weight of the polymer produced in the whole process, preferably it ranges from 30% to 90% by weight and more preferably from 35% to 75% by weight.

The polymer obtained in step b1) can optionally contains up to 20% by mol of a non conjugated diene. Non conjugated dienes can be a straight chain, branched chain or cyclic hydrocarbon diene having from 6 to 20 carbon atoms. Examples of suitable non-conjugated dienes are:

straight chain acyclic dienes, such as 1,4-hexadiene and 1,6-octadiene;
branched chain acyclic dienes, such as 5-methyl-1,4-hexadiene, 3,7-dimethyl-1,6-octadiene, 3,7-dimethyl-1,7-octadiene and mixed isomers of dihydro myricene and dihydroocinene;
single ring alicyclic dienes, such as 1,3-cyclopentadiene, 1,4-cyclohexadiene, 1,5-cyclooctadiene and 1,5-cyclododecadiene;
multi-ring alicyclic fused and bridged ring dienes, such as tetrahydroindene, methyl tetrahydroindene, dicyclopentadiene, bicyclo-(2,2,1)-hepta-2,5-diene; and
alkenyl, alkylidene, cycloalkenyl and cycloalkylidene norbornenes, such as 5-methylene-2-norbornene (MNB), 5-propenyl-2-norbornene, 5-isopropylidene-2-norbornene, 5-(4-cyclopentenyl)-2-norbornene, 5-cyclohexylidene-2-norbornene, 5-vinyl-2-norbornene and norbornadiene.

Preferred dienes are 1,4-hexadiene (HD), 5-ethylidene-2-norbornene (ENB), 5-vinylidene-2-norbornene (VNB), 5-methylene-2-norbornene (MNB) and dicyclopentadiene (DCPD). Particularly preferred dienes are 5-ethylidene-2-norbornene (ENB) and 1,4-hexadiene (HD). When present the non-conjugated dienes are preferably incorporated into the polymer in an amount from 0.1% to about 20% by mol, preferably from 0.5% to 15% by mol, and more preferably from 0.5% to 7% by mol. If desired, more than one diene may be incorporated simultaneously, for example HD and ENB, with total diene incorporation within the limits specified above.

The processes of the present invention can be carried out in one reactor or in two or more reactors in series.

Further object of the present invention is a ligand of formula (III)

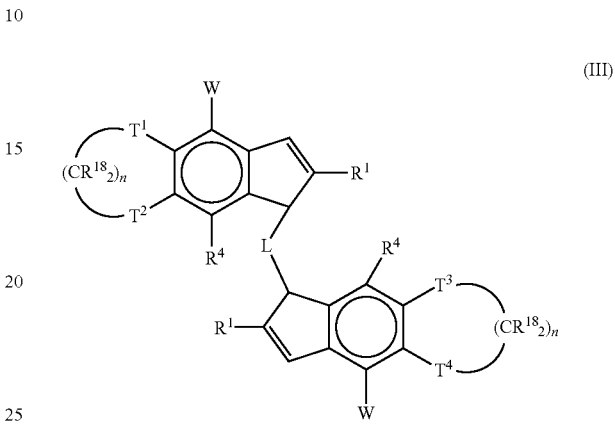

or its double bond isomers wherein L, $R^1$, $R^4$, $T^1$, $T^2$, $T^3$, $T^4$ and W have the meaning reported above.

Preferred ligands have formulas (IIIa), (IIIb), (IIIc) or (IIId):

(IIIa)

(IIIb)

-continued

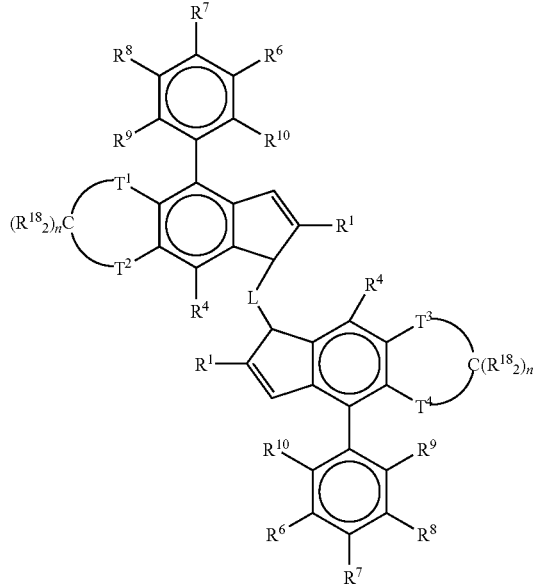

(IIIc)

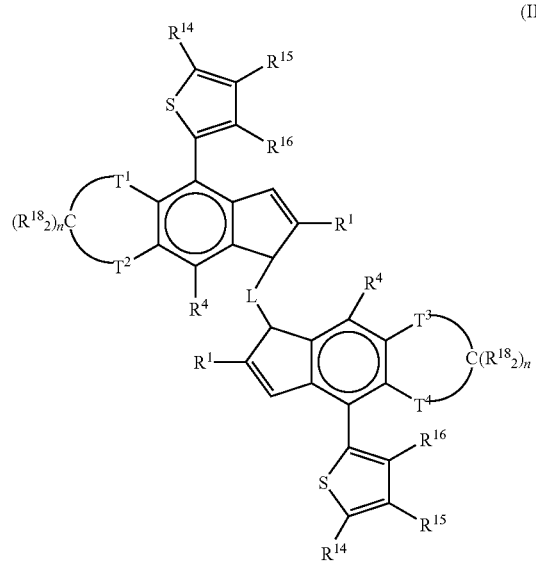

(IIId)

or their double bond isomers wherein L, W, n, $R^1$-$R^{18}$ have the meaning reported above.

The metallocene compounds of formula (I) can be obtained with a process comprising the steps of reacting the dianion with a suitable transition metal source such as metal tetrahalide as for example zirconium tetrachloride. The dianion can be obtained for example by the deprotonation of the ligand of formula (III), for example by using an organolithium compound such as butyl or methyl lithium.

The ligand of formula (III) can be easily prepared starting from the cyclopentadienyl moieties of formulas (IV) and (V)

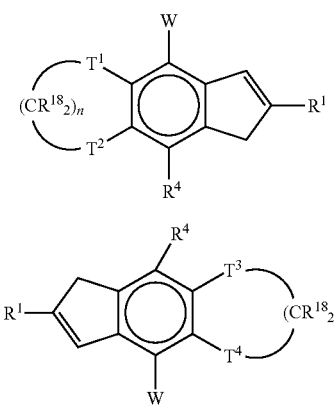

(IV)

(V)

wherein $T^1$, $T^2$, $T^3$, $T^4$, $R^1$, $R^4$, $R^{18}$ and W have the meaning described above with a process comprising the following steps:

a) Contacting the compound of formula (IV) and/or its double bond isomers with a base selected from $T^5_jB$, $T_5MgT^6$, sodium and potassium hydride, metallic sodium and potassium; wherein $T^5$, j, B and $T^6$ are defined as above, and wherein the molar ratio between said base and the compound of the formula (IV) is at least 1:1; excess of said base can be used;

b) contacting the anionic compound obtained in step a) with a compound of formula $LY^2$ wherein L is defined as above and Y is chlorine, bromine and iodine, preferably Y is chlorine or bromine; to form a compound of formula (IVa)

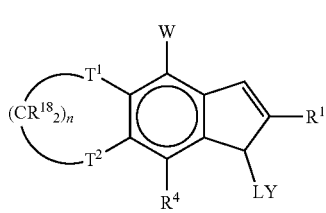

(IVa)

c) contacting the compound of formula (IVa) with the anionic derivative of compound of formula (V) obtained as described in step a).

in case of C2 symmetric compounds the process described above can be carried out also "one pot" by reacting a calculate amount of the compound of formula $LY_2$ with the dianionic derivative formed in step a).

The above processes are preferably carried out in an aprotic solvent, either polar or apolar. Said aprotic solvent is preferably an aromatic or aliphatic hydrocarbon, optionally halogenated, or an ether; more preferably it is selected from benzene, toluene, pentane, hexane, heptane, cyclohexane, dichloromethane, diethylether, tetrahydrofurane and mixtures thereof. The above process is carried out at a temperature ranging from −100° C. to +80° C., more preferably from −20° C. to +70° C.

The following examples are given to illustrate and not to limit the invention.

EXAMPLES

General Characterization

Intrinsic Viscosity (IV) in Tetrahydronaphthalene

The measurement for examples 1-5 were done in tetrahydronaphtalene (THN) solution obtained by dissolving the polymer at 135° C. for 1 hour.

$^{13}$C-NMR Measurement

The chemical composition and comonomer distribution of the copolymers were investigated by 13C-NMR analysis with a Bruker DPX400 spectrometer operating at 100.61 MHz. The samples were measured as 8% (w/v) solutions of 1,1,2,2-tetrachloroethane, the 13C-NMR spectra were recorded at 120° C. with a 90 degree pulse, 12 s of delay between pulses and CPD to remove 1H-13C coupling. About 1K of transients were stored in 32K data points using a spectral window of 6000 Hz. The Sδδ peak at 29.9 ppm (nomenclature according to reference 1) was used as internal reference. The product of reactivity ratios r1×r2 was calculated from the triads according to reference 1. The copolymer compositions and triad distributions were determined according to reference 2.

reference 1: Carman, C. J.; Harrington, R. A.; Wilkes, C. E. Macromolecules 1977, 10, 563 reference 2: Kakugo, M.; Naito, Y,; Mizunuma, K. Macromolecules 1982, 15, 1150.

Chemicals and Characterization

All chemicals were handled using standard Schlenk techniques.

Methylalumoxane (MAO) was received from Albemarle as a 30% wt/V toluene solution and used as such and the silica was received from INEOS (ES70Y, 100 microns).

Synthesis of μ-{Bis-[η$^5$-8-(4-tert-butylphenyl)-6-methyl-5H-indeno[5,6-a][1,3]dioxol-5-yl]dimethylsilanediyl}dichlorozirconium (IV) (A-1)

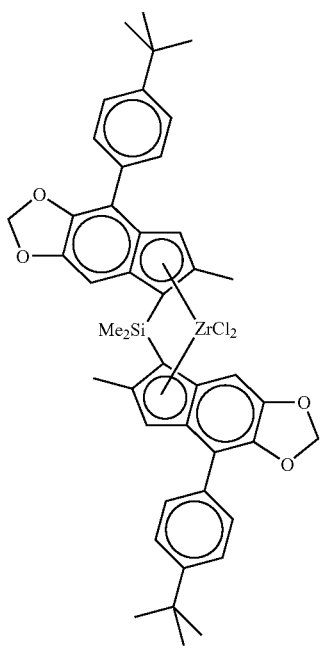

Synthesis of 5-(Chloromethyl)-1,3-benzodioxole

Piperonyl alcohol (45.64 g, 300 mmol) was dissolved in 340 ml of dry benzene, and SOCl$_2$ (37 ml) was added dropwise with stirring. The solution was refluxed for 1 h, cooled and evaporated on the rotary evaporator (bath temperature less than 50° C.!). The resulting dark green residue was used without further purification.

$^1$H NMR (CDCl$_3$, 20° C.) δ: 6.90 (s, 1H); 6.87 (d, 1H); 6.79 (d, 1H) {C$_{Ar}$—H}; 5.98 (s, 2H, —OCH$_2$O—); 4.54 (s, 2H, —CH$_2$Cl).

Synthesis of 2-(1,3-Benzodioxol-5-ylmethyl)-2-methylmalonic acid and 3-(1,3-benzodioxol-5-yl)-2-methylpropanoic acid Diethyl 2-methylmalonate (57.5 g, 330 mmol) was added to a hot solution of EtONa (from 7.58 g, 330 mmol of Na and 250 ml of ethanol) and the reaction mixture was stirred for 30 min. The previously obtained 5-(chloromethyl)-1,3-benzodioxole (300 mmol) in EtOH (40 ml) was added dropwise, the resulting mixture was refluxed for 6 h and stirred overnight. KOH (51 g) in H$_2$O (85 ml) was added, and the mixture was refluxed for 4 h. The volatiles were removed under reduced pressure, the residue was dissolved in water (500 ml), extracted with hexane (2×100 ml), the water layer was acidified (HCl) to pH ~1. Crystalline acid was filtered off, washed with cold water and dried in vacuo.

$^1$H NMR (DMSO-d$_6$, 20° C.) δ: 13.0-12.5 (broad, —COOH); 6.77 (d, 1H); 6.69 (s, 1H); 6.62 (d, 1H) {C$_{Ar}$—H}; 5.94 (s, 2H, —OCH$_2$O—); 2.99 (s, 2H, —CH$_2$—) 1.15 (s, 3H, —CH$_3$).

$^{13}$C NMR (DMSO-d$_6$, 20° C.) δ: 173.4 (—COOH); 147.2; 146.3; 130.6 (>C═); 123.0; 110.0; 107.6 (—CH═); 100.6 (—OCH$_2$O—); 53.8; 20.1; 18.8 (—CH$_2$—, >C< and —CH$_3$).

Resulting 2-(1,3-benzodioxol-5-ylmethyl)-2-methylmalonic acid was heated to 170-180° C. for 10 min. The residue was practically pure 3-(1,3-benzodioxol-5-yl)-2-methylpropanoic acid (47.58 g, yield 76.2% based on piperonyl alcohol).

$^1$H NMR (CDCl$_3$, 20° C.) δ: 11.5-11.0 (broad, —COOH); 6.75 (d, 1H); 6.70 (s, 1H); 6.66 (d, 1H) {C$_{Ar}$—H}; 5.95 (s, 2H, —OCH$_2$O—); 3.00 (m, 1H); 2.72 (m, 1H); 2.61 (m, 1H) {>CHCH$_2$—}; 1.19 (d, 3H, —CH$_3$).

$^{13}$C NMR (CDCl$_3$, 20° C.) δ: 182.5 (—COOH); 147.6; 146.0; 132.7 (>C═); 121.9; 109.3; 108.1 (—CH═); 100.8 (—OCH$_2$O—); 41.5 (>CH—); 39.0 (—CH$_2$—); 16.4 (—CH$_3$).

Synthesis of 6-Methyl-6,7-dihydro-5H-indeno[5,6-d][1,3]dioxol-5-one

The acid obtained above (47.58 g, 228.5 mmol) was dissolved in dry benzene (450 ml), and SOC$_2$ (56 ml) was added. The resulting mixture was stirred for 0.5 h at room temperature, refluxed for additional 3 h and evaporated. The residue was dissolved in CH$_2$Cl$_2$ (470 ml), cooled to 0° C., and SnCl$_4$ (34 ml, 290 mmol) in CH$_2$Cl$_2$ (180 ml) was added. The reaction mixture was allowed to warm to room temperature, stirred for 30 min, poured into ice/HCl (300 ml), and extracted with CH$_2$Cl$_2$ (6×100 ml). The combined organic fractions were dried over MgSO$_4$, passed through SiO$_2$ and evaporated giving solid product. Yield 43.4 g (100%).

$^1$H NMR (CDCl$_3$, 20° C.) δ: 7.08 (s, 1H); 6.81 (s, 1H) {C$_{Ar}$—H}; 6.07 (s, 2H, —OCH$_2$O—); 3.28 (m, 1H); 2.70 (m, 1H); 2.61 (m, 1H) {>CHCH$_2$—}; 1.29 (d, 3H, —CH$_3$).

$^{13}$C NMR (CDCl$_3$, 20° C.) δ: 207.6 (>C=O); 154.4; 151.1; 148.4; 130.9 (>C=); 105.8; 102.6 (—CH=); 102.3 (—OCH$_2$O—); 42.6 (>CH—); 35.1 (—CH$_2$—); 16.8 (—CH$_3$).

Synthesis of 8-Bromo-6-methyl-6,7-dihydro-5H-indeno[5,6-d][1,3]dioxol-5-one

Br$_2$ (11.42 ml, 221.44 mmol) was added dropwise at 0° C. into well stirred mixture of 6-ethyl-6,7-dihydro-5H-indeno[5,6-d][1,3]dioxol-5-one (40.01 g, 210.37 mmol) solution in CH$_2$Cl$_2$ (93 ml) and NaOAc (35.32 g, 430 6 mmol) solution in water (62 ml). After 20 h of stirring at room temperature, 11.5 g of AcONa and 3.42 ml of Br$_2$ (30% of starting amount) were added. This procedure was repeated after 24 h, the resulting mixture was stirred for additional 48 h. The resulting mixture was diluted by CH$_2$Cl$_2$ (200 ml), the organic layer was separated, washed with water (350 ml), dried over MgSO$_4$ and evaporated. The residue was recrystallized from hexane-benzene (3:1) yielding 32.83 g (58%) of white-yellow solid.

$^1$H NMR (CDCl$_3$, 20° C.) δ: 7.07 (s, 1H, C$_{Ar}$—H); 6.16 (s, 21H, —OCH$_2$O—); 3.26 (m, 1H); 2.75 (m, 1H); 2.57 (m, 1H) {>CHCH$_2$—}; 1.33 (d, 3H, —CH$_3$).

$^{13}$C NMR (CDCl$_3$, 20° C.) δ: 204.5 (>C=O); 152.0; 150.1; 148.5; 132.2; 99.5 (>C=); 102.6; (—CH=); 101.8 (—OCH$_2$O—); 42.3 (>CH—); 35.2 (—CH$_2$—); 16.4 (—CH$_3$).

Synthesis of 8-(4-tert-Butylphenyl)-6-methyl-6,7-dihydro-5H-indeno[5,6-d][1,3]dioxol-5-one Pd(OAc)$_2$ (0.82 g, 3.66 mmol) and PPh$_3$ (1.92 g, 7.32 mmol) were added to well stirred mixture of 8-bromo-6-methyl-6,7-dihydro-5H-indeno[5,6-d][1,3]dioxol-5-one (32.83 g, 122 mmol), tert-butylphenylboronic acid (28.34 g, 158.6 mmol) and Na$_2$CO$_3$ (33.62 g, 317.2 mmol) in DME (375 ml)/H$_2$O (125 ml). The resulting mixture was refluxed with stirring for 8 h, cooled, poured into water and extracted with CH$_2$Cl$_2$ (5×150 ml). The combined organic phase was washed with aq. Na$_2$CO$_3$, water, dried over MgSO$_4$, evaporated and purified from di-tert-butylbiphenyl by simple chromatography on silica gel (eluent benzene; then Et$_2$O), and dried in vacuo. Yield 30.63 g (77.9%).

$^1$H NMR (CDCl$_3$, 20° C.) δ: 7.56 (d, 2H); 7.49 (d, 2H); 7.18 (s, 1) {C$_{Ar}$—H}; 6.10 (s, 1H); 6.09 (s, 1H) {-OCH$_2$O—}; 3.33 (m, 1H); 2.73 (m, 1H); 2.65 (m, 1H) {>CHCH$_2$—}; 1.44 (s, 9H, —C(CH$_3$)$_3$); 1.33 (d, 3H, —CH$_3$).

$^{13}$C NMR (CDCl$_3$, 20° C.) δ: 207.4 (>C=O); 151.1; 148.9; 148.4; 131.3; 130.0; 120.8; 97.7 (>C=); 128.7; 128.2; 125.4 (—CH=); 101.9 (—OCH$_2$O—); 42.4 (>CH—); 34.6; 34.5 (—CH$_2$— and >C<); 31.2; 16.4 (—CH$_3$).

Synthesis of 4-(4-tert-Butylphenyl)-6-methyl-5H-indeno[5,6-d][1,3]dioxole 8-(4-tert-Butylphenyl)-6-methyl-6,7-dihydro-5H-indeno[5,6-d][1,3]dioxol-5-one (30.63 g, 95 mmol) in Et$_2$O (200 ml) was added to a cooled (−40° C.) suspension of LiAlH$_4$ (1.08 g, 28.5 mmol) in Et$_2$O (60 ml). The resulting mixture was allowed to warm to room temperature and stirred for additional 1.5 h. Then 2% HCl (100 ml) was added, the resulting mixture was extracted with CH$_2$Cl$_2$ (4×100 ml). The organic phase was washed with water, dried over MgSO$_4$ and evaporated. The flask was sparged with argon; benzene (300 ml) and p-TSA (0.2 g) were added, and the resulting solution was refluxed with Dean-Stark head (control by TLC, benzene) for 2 h. Then the resulting yellow solution was washed with water, aq. KHCO$_3$, water, dried over MgSO$_4$, passed through silica gel and evaporated. The residue was recrystallized from hexane —Et$_2$O (ca. 10:1) yielding 19.7 g (67.7%) of white crystalline product.

$^1$H NMR (CDCl$_3$, 20° C.) δ: 7.57 (d, 2H); 7.52 (d, 2H); 6.80 (s, 1H) {C$_{AR}$—H}; 6.45 (s, 1H, =CH—); 5.98 (s, 2H, —OCH$_2$O—); 3.33 (s, 2H, —CH$_2$—); 2.14 (s, 3H, —CH$_3$); 1.41 (s, 9H, —C(CH$_3$)$_3$).

$^{13}$C NMR (CDCl$_3$, 20° C.) δ: 150.3; 146.6; 145.0; 139.9; 134.9; 132.2; 120.4; 97.1 (>C=); 128.5; 126.7; 125.3; 100.2 (—CH=); 100.7 (—OCH$_2$O—); 42.4 (—CH$_2$—); 34.6 (>C<); 31.3; 16.7 (—CH$_3$).

Synthesis of Bis[8-(4-tert-butylphenyl)-6-methyl-5H-indeno[5,6-d][1,3]dioxol-5-yl](dimethyl)silane A solution of 4-(4-tert-butylphenyl)-6-methyl-5H-indeno[5,6-d][1,3]dioxole (6.13 g, 20 mmol) in Et$_2$O (60 ml) was cooled to −40° C., and n-BuLi in hexane (1.6M, 12.9 ml, 20.6 mmol) was added. The resulting mixture was allowed to warm to room temperature, stirred for 3 h, cooled to −60° C., and CuCN (54 mg, 0.6 mmol) was added. After 15 min SiMe$_2$Cl$_2$ (1.23 ml, 10.2 mmol) was added. The resulting mixture was allowed to warm to room temperature, and stirred for 16 h. H$_2$O (10 ml) and benzene (200 ml) were added, the organic phase was separated, dried over MgSO$_4$, passed through silica gel and evaporated. The residue was dried in vacuo (pale-yellow solid) and used without purification.

$^1$H NMR (CDCl$_3$, 20° C.) δ: 7.56 (m, 6H); 7.69-7.54 (group of d, 8H); 7.00 (s); 6.99 (s) (2H) {C$_{Ar}$—H}; 6.82 (bs); 6.81 (bs) {2H, —CH=}; 6.04 (m, 4H, —OCH$_2$O—); 3.78 (s); 3.76 (s) {2H, >H}; 2.30 (bs); 2.28 (bs) {6H, —C—CH$_3$}; 1.49 (s); 1.48 (s) {18K, —C(CH$_3$)$_3$}; −0.07 (s); −0.10 (s) {6H, Si—CH$_3$}.

Synthesis of μ-{Bis-[η$^5$-8-(4-tert-butylphenyl)-6-methyl-5H-indeno[5,6-d][1,3]dioxol-5-yl] dimethylsilanediyl}dichlorozirconium (IV) (A-1)

Bis[8-(4-tert-butylphenyl)-6-methyl-5H-indeno[5,6-d][1,3]dioxol-5-yl](dimethyl)silane (3.35 g, 5 mmol) was dissolved in Et$_2$O (40 ml), cooled to −40° C., and n-BuLi (1.6M in hexane, 6.6 ml, 10.5 mmol) was added. The reaction mixture was allowed to warm to room temperature, stirred for 3 h, and evaporated. The resulting yellow powder was suspended in pentane (80 ml), cooled to −60° C., and ZrCl$_4$ (1.28 g, 5.5 mmol) was added. After 5 min Et$_2$O (0.5 ml) was added. The resulting mixture was allowed to warm to room temperature, stirred for additional 16 h, and filtered. The so obtained orange-yellow powder was dried and recrystallized from DME. The resulting orange precipitate was washed with Et 20 (4×50 ml); the residue was recrystallized from Et$_2$O/CH$_2$Cl$_2$ (3:1) yielding the racemic product (0.28 g, 13.5%).

$^1$H NMR (CDCl$_3$, 20° C.) δ: 7.69 (d, 4H); 7.51 (d, 4H); 6.94 (s, 2H); 6.90 (s, 2H) {C$_{Ar}$—H}; 6.06 (d, 2H); 5.98 (d, 2H) {-OCH$_2$O—}; 2.27 (s, 6H, C—CH$_3$); 1.38 (s, 18H, —C(CH$_3$)$_3$); 1.28 (s, 6H, Si—CH$_3$).

rac-Dimethylsilylbis(2-methyl-4-phenyl-indenyl)zirconiumdichloride (C-1) was prepared according to EP 576970 rac-dimethylsilylbis(2-methyl-4-(para-tert-butylphenyl)-indenyl)-zirconium dichloride (rac-Me$_2$Si(2-Me-4(4tBuPh)Ind)$_2$ZrCl$_2$) (C-2) was prepared according to WO 98/40331 (example 65).

Preparation of the Catalyst Systems

Catalyst System CA-1

A-1/MAO:TIBA 2.4:1 ($Al_{TOT}$/Zr=455):

9.5 mL of TIBA/isododecane solution (110 g/L) were mixed with 2.7 mL of MAO/toluene solution (Albemarle 30% wt/wt, d=0.92 g/mL, 12.8 mmol MAO) to obtain a MAO/TIBA molar ratio of 2.4:1. The solution was stirred for 60 minutes at room temperature and transferred into a 50 mL Schlenk flask containing A-1 (33 mg, 39.8 µmol). The resulting dark red mixture was diluted with 5.1 mL of toluene. The color of the mixture resulted slightly lighter after one week, but still contained some suspension. Concentration of the final solution: 105 $g_{TOT}$/L and 1.9 $g_{metallocene}$/L.

Catalyst System CC-1

C-1/MAO:TIBA 1.8:1 ($Al_{TOT}$/Zr=378):

21.1 mL of TIBA/isododecane solution (110 g/L) were mixed with 4.5 mL of MAO/toluene solution (Albemarle 30% wt/wt, d=0.92 g/mL, 21.6 mmol MAO) to obtain a MAO/TIBA molar ratio of 1.8:1. The solution was stirred for 1 h at room temperature. Then, 55.3 mg of C-1 were dissolved in the solution. The solution did not show any trace of residual solid. The final solution was diluted with 11.7 mL of isododecane to reach a concentration of 97 $g_{TOT}$/L and 1.48 $g_{metallocene}$/L.

After 3 weeks the solution showed same aspect and color (dark red) as originally prepared.

Catalyst System CC-2

C-2/MAO:TIBA 1.8:1 ($Al_{TOT}$/Zr=378):

17 mL of TIBA/isododecane solution (110 g/L) were mixed with 3.7 mL of MAO/toluene solution (Albemarle 30% wt/wt, d=0.92 g/mL, 17.6 mmol MAO) to obtain a MAO/TIBA molar ratio of 1.8:1. The solution was stirred for 1 h at room temperature. Then, 52.6 mg of C-2 were dissolved in the solution. The solution did not show any trace of residual solid. The final solution was diluted with 9.5 mL of isododecane to reach a concentration of 98 $g_{TOT}$/L and 1.74 $g_{metallocene}$/L.

After 3 weeks the solution showed same aspect and color (dark red) as originally prepared.

Polymerization Tests

Comparative Example 1

A 4.4 L jacketed stainless-steel autoclave, equipped with a magnetically driven stirrer and a 35-mL stainless-steel vial and connected to a thermostat for temperature control, was previously purified by washing with an Al(i-Bu)$_3$ solution in hexane and dried at 50° C. in a stream of nitrogen.

6 mmol of Al(i-Bu)$_3$ (as a 100 g/L solution in hexane), 735 g of cyclo-hexane, 41 g of ethylene and 652 g of propylene were charged at room temperature, in order to obtain in the polymerization conditions, a liquid composition of 5/95 ethylene/propylene (wt/wt). The autoclave was then thermostated at the polymerization temperature, 90° C., corresponding for this composition at a pressure of 28 bar-g.

4 mL of the catalyst system CC-1 containing the catalyst/cocatalyst mixture (1.48 mg metallocene/mL solution) was injected in the autoclave by means of 4 mL of c-hexane through the stainless-steel vial. A constant ethylene/propylene mixture 10/90% wt was continuously fed for 30 minutes to maintain the pressure at 28 bar-g for a total consumption of 14 grams of ethylene and 123 grams of propylene.

The pressure into the autoclave was decreased until 20 bar, the bottom discharge valve was opened and the copolymer was discharged into a heated steel tank containing water at 70° C. The tank heating was switched off and a flow of nitrogen at 0.5 bar-g was fed. After cooling at room temperature, the steel tank was opened and the wet polymer collected. The wet polymer was dried in an oven under reduced pressure at 70° C.

Comparative Example 2

The procedure of comparative example 1 was repeated feeding 731 g of c-hexane, 73 g of ethylene and 622 g of propylene in order to obtain a liquid composition at 90° C., 32 barg, corresponding to a liquid composition of 9/91% wt ethylene/propylene.

4 mL of the catalyst system CC-1 containing the catalyst/cocatalyst mixture (1.48 mg metallocene/mL solution) was injected in the autoclave by means of 4 mL of cyclohexane through the stainless-steel vial.

A mixture of ethylene/propylene 17/83% wt was continuously fed for 30 minutes to maintain the pressure of 32 bar-g: 12.2 g of ethylene and 58.2 g of propylene were consumed.

The copolymer was discharged according to the procedure described in the comparative example 1. The polymerization data are reported in table 1.

Comparative Example 3

The procedure of comparative example 1 was repeated feeding 735 g of c-hexane, 41 g of ethylene and 652 g of propylene in order to obtain a liquid composition at 90° C., 28 bar-g, corresponding to a liquid composition of 5/95% wt ethylene/propylene.

4 mL of the catalyst system CC-2 containing the catalyst/cocatalyst mixture (1.74 mg metallocene/mL solution) was injected in the autoclave by means of 4 mL of cyclohexane through the stainless-steel vial.

A mixture of ethylene/propylene 10/90% wt was continuously fed for 30 minutes to maintain the pressure of 28 barg: 10 g of ethylene and 88 g of propylene were consumed.

The copolymer was discharged according to the procedure described in the comparative example 1. The polymerization data are reported in table 1.

Comparative Example 4

The procedure of comparative example 1 was repeated feeding 731 g of c-hexane, 73 g of ethylene and 622 g of propylene in order to obtain a liquid composition at 90° C., 32 barg, corresponding to a liquid composition of 9/91% wt ethylene/propylene.

4 mL of the catalyst system CC-2 containing the catalyst/cocatalyst mixture (1.74 mg metallocene/mL solution) was injected in the autoclave by means of 4 mL of cyclohexane through the stainless-steel vial.

A mixture of ethylene/propylene 25/75% wt was continuously fed for 30 minutes to maintain the pressure of 32 barg: 17.2 g of ethylene and 52.3 g of propylene were consumed.

The copolymer was discharged according to the procedure described in the comparative example 1. The polymerization data are reported in table 1.

Example 5

The procedure of comparative example 1 was repeated feeding 735 g of c-hexane, 41 g of ethylene and 652 g of propylene in order to obtain a liquid composition at 90° C., 28 bar-g, corresponding to a liquid composition of 5/95% wt ethylene/propylene.

1 mL of the catalyst system CA-1 containing the catalyst/cocatalyst mixture (1.9 mg metallocene/mL solution) was injected in the autoclave by means of 4 mL of cyclohexane through the stainless-steel vial.

A mixture of ethylene/propylene 10/90% wt was continuously fed for 30 minutes to maintain the pressure of 28 bar-g: 9.4 g of ethylene and 86 g of propylene were consumed.

The copolymer was discharged according to the procedure described in the comparative example 1. The polymerization data are reported in table 1.

Example 6

The procedure of comparative example 1 was repeated feeding 731 g of c-hexane, 73 g of ethylene and 622 g of propylene in order to obtain a liquid composition at 90° C., 32 bar-g, corresponding to a liquid composition of 9/91% wt ethylene/propylene.

1 mL of the catalyst system CA-1 containing the catalyst/cocatalyst mixture (1.9 mg metallocene/mL solution) was injected in the autoclave by means of 4 mL of cyclohexane through the stainless-steel vial.

A mixture of ethylene/propylene 17/83% wt was continuously fed for 30 minutes to maintain the pressure of 32 bar-g: 7.8 g of ethylene and 37.3 g of propylene were consumed.

The copolymer was discharged according to the procedure described in the comparative example 1. The polymerization data are reported in table 1.

TABLE 1

| Ex | Catalyst System | Yield (g) | $kg_{POL}/(g_{met}*h')$ | I.V. (THN) dL/g | Ethylene from NMR (% wt) | Propylene from NMR (% wt) | $r_1 r_2$ |
|---|---|---|---|---|---|---|---|
| 1 | CC-1 | 320 | 92.6 | 1.1 | 11.3 | 88.7 | 2.8 |
| 2 | CC-1 | 187 | 54.2 | 1.2 | 17.1 | 82.9 | 2.3 |
| 3 | CC-2 | 257 | 63.4 | 1.3 | 10.1 | 89.9 | 2.4 |
| 4 | CC-2 | 273 | 67.2 | 1.5 | 12.5 | 87.5 | 3.1 |
| 5 | CA-1 | 412 | 359.6 | 1.2 | 7.4 | 92.6 | 1.7 |
| 6 | CA-1 | 231 | 241.8 | 1.3 | 17.1 | 82.9 | 1.6 |

As can be seen from table 1, the activity of the catalyst system of the present invention is considerably higher than those of the comparative example while a quite high molecular weight is retained.

The invention claimed is:

1. A bridged metallocene compound of formula (I)

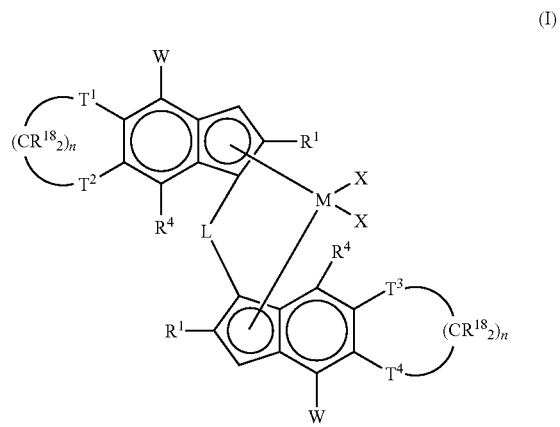

wherein:

M is an atom of a transition metal selected from group 4 or the actinide group in the Periodic Table of Elements;

X, equal to or different from each other, is hydrogen, a halogen, R, OR, $OSO_2CF_3$, OCOR, SR, $NR_2$, or $PR_2$, or two X groups can be joined to form OR'O;

R is a linear or branched, cyclic or acyclic, $C_1$-$C_{40}$-alkyl, $C_2$-$C_{40}$ alkenyl, $C_2$-$C_{40}$ alkynyl, $C_6$-$C_{40}$-aryl, $C_7$-$C_{40}$-alkylaryl or $C_7$-$C_{40}$-arylalkyl, optionally comprising at least one heteroatom belonging to groups 13-17 of the Periodic Table of Elements;

R' is a $C_1$-$C_{20}$-alkylidene, $C_6$-$C_{20}$-arylidene, $C_7$-$C_{20}$-alkylarylidene, or $C_7$-$C_{20}$-arylalkylidene radical;

L is a divalent bridging group selected from a $C_1$-$C_{20}$ alkylidene, a $C_3$-$C_{20}$ cycloalkylidene, a $C_6$-$C_{20}$ arylidene, a $C_7$-$C_{20}$ alkylarylidene, or a $C_7$-$C_{20}$ arylalkylidene, optionally comprising at least one heteroatom belonging to groups 13-17 of the Periodic Table of Elements, or L is a silylidene radical comprising up to 5 silicon atoms;

$R^1$ is a linear $C_1$-$C_{40}$ hydrocarbon, optionally comprising at least one heteroatom belonging to groups 13-17 of the Periodic Table of Elements;

$T^1$ and $T^2$, equal to or different from each other, are oxygen, sulfur, or $C(R^{18})_2$, with the proviso that at least one of $T^1$ and $T^2$ is oxygen or sulfur;

$R^{18}$, equal to or different from each other, are hydrogen or a $C_1$-$C_{40}$ hydrocarbon, optionally comprising at least one heteroatom belonging to groups 13-17 of the Periodic Table of Elements;

n is 1, 2 or 3;

$T^3$ and $T^4$, equal to or different from each other, are oxygen, sulfur, or $C(R^{18})_2$;

$R^4$ is hydrogen, or a $C_1$-$C_{40}$ hydrocarbon optionally comprising at least one heteroatom belonging to groups 13-17 of the Periodic Table of Elements;

W is an aromatic 5 or 6 membered ring optionally comprising at least one heteroatom belonging to groups 15-16 of the Periodic Table of Elements, wherein the valence of each atom of said 5 or 6 membered ring is substituted with hydrogen, or is optionally substituted with at least one $R^5$; and $R^5$, equal to or different from each other, is a $C_1$-$C_{40}$ hydrocarbon, optionally comprising at least one heteroatom belonging to groups 13-17 of the Periodic Table of Elements.

2. The bridged metallocene compound according to claim 1, wherein

M is zirconium, titanium or hafnium;

X is hydrogen, a halogen, OR'O, or R;

L is $Si(R^{11})_2$; and $R^{11}$ is a linear or branched, cyclic or acyclic $C_1$-$C_{40}$-alkyl, $C_2$-$C_{40}$ alkenyl, $C_2$-$C_{40}$ alkynyl, $C_6$-$C_{40}$-aryl, $C_7$-$C_{40}$-alkylaryl, or $C_7$-$C_{40}$-arylalkyl.

3. The bridged metallocene compound according to claim 1, wherein W is selected from the group consisting of formula (Wa), (Wb) and (Wc):

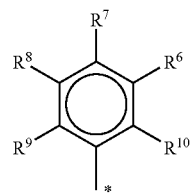

(Wa)

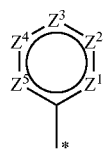

(Wb)

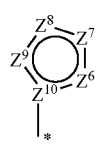

(Wc)

wherein * represents the point in which the moiety is bound to the indenyl moiety of the compound of formula (I);

$R^6$, $R^7$, $R^8$, $R^9$ and $R^{10}$, equal to or different from each other, are hydrogen or $C_1$-$C_{40}$ hydrocarbons, optionally comprising at least one heteroatom belonging to groups 13-17 of the Periodic Table of Elements;

$Z^1$ is nitrogen or $CR^{10}$;

$Z^2$ is nitrogen or $CR^6$;

$Z^3$ is nitrogen or $CR^7$;

$Z^4$ is nitrogen or $CR^8$;

$Z^5$ is nitrogen or $CR^9$, with the proviso that no more than 2 groups selected from $Z^1$, $Z^2$, $Z^3$, $Z^4$ and $Z^5$ are nitrogen;

$Z^6$ is oxygen, sulfur, $NR^{13}$ or $CR^{13}$;

$Z^7$ is oxygen, sulfur, $NR^{14}$ or $CR^{14}$;

$Z^8$ is oxygen, sulfur, $NR^{15}$ or $CR^{15}$;

$Z^9$ is oxygen, sulfur, $NR^{16}$ or $CR^{16}$;

$Z^{10}$ is a nitrogen or carbon that bonds to the indenyl moiety of the structure of formula (I), with the proviso that not more than 1 group among $Z^6$, $Z^7$, $Z^8$, $Z^9$ or $Z^{10}$ is sulfur, oxygen, nitrogen, or a nitrogen-containing group selected from $NR^{13}$, $NR^{14}$, $NR^{15}$, or $NR^{16}$; and $R^{13}$, $R^{14}$, $R^{15}$ and $R^{16}$, equal to or different from each other, are hydrogen or $C_1$-$C_{40}$ hydrocarbons optionally comprising at least one heteroatom belonging to groups 13-17 of the Periodic Table of Elements.

4. The bridged metallocene compound according to claim 3, wherein in the moiety of formula (Wa), $R^7$ is a $C_1$-$C_{40}$-alkyl, and $R^6$, $R^8$, $R^9$ and $R^{10}$ are hydrogen.

5. The bridged metallocene compound according to claim 3, wherein in the moiety of formula (Wa), $R^{10}$ and $R^8$, equal to or different, are a $C_1$-$C_{40}$-alkyl, and $R^6$, $R^7$ and $R^9$ are hydrogen.

6. The bridged metallocene compound according to claim 3, wherein in the moiety of formula (Wa), $R^6$, $R^7$ and $R^8$, equal to or different, are linear or branched $C_1$-$C_{40}$-alkyls, and $R^{10}$ and $R^9$, equal to or different, are hydrogen.

7. The bridged metallocene compound according to claim 3, wherein in the moiety of formula (Wa), $R^6$, $R^7$, $R^8$, $R^9$ and $R^{10}$ are hydrogen.

8. The bridged metallocene compound according to claim 3, wherein in the moiety of formula (Wb), $Z^1$ is nitrogen, and $Z^2$, $Z^3$, $Z^4$ and $Z^5$ are respectively $CR^6$, $CR^7$, $CR^8$ and $CR^9$.

9. The bridged metallocene compound according to claim 3, wherein in the moiety of formula (Wb), $Z^3$ is nitrogen, and $Z^1$, $Z^2$, $Z^4$ and $Z^5$ are respectively $CR^{10}$, $CR^6$, $CR^8$ and $CR^9$.

10. The bridged metallocene compound according to claim 3, wherein in the moiety of formula (Wb), $Z^2$ is nitrogen, and $Z^1$, $Z^3$, $Z^4$ and $Z^5$ are respectively $CR^{10}$, $CR^7$, $CR^8$ and $CR^9$.

11. A bridged metallocene compound of formula (Ia):

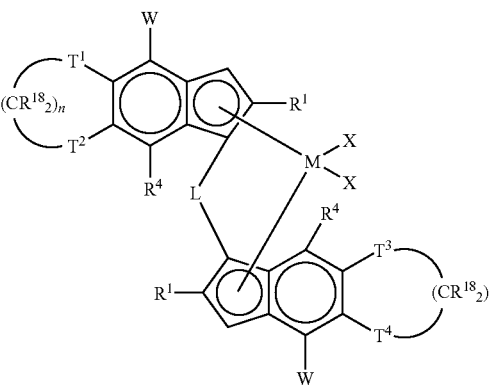

(Ia)

wherein $T^1$, $T^2$, $T^3$ and $T^4$ are oxygen or sulfur;

n is 1 or 2;

M is an atom of a transition metal selected from group 4 or the actinide group in the Periodic Table of Elements;

L is a divalent bridging group selected from a $C_1$-$C_{20}$ alkylidene, a $C_3$-$C_{20}$ cycloalkylidene, a $C_6$-$C_{20}$ arylidene, a $C_7$-$C_{20}$ alkylarylidene, or a $C_7$-$C_{20}$ arylalkylidene, optionally comprising at least one heteroatom belonging to groups 13-17 of the Periodic Table of Elements, or L is a silylidene radical comprising up to 5 silicon atoms;

X, equal to or different from each other, is hydrogen, a halogen, R, OR, $OSO_2CF_3$, OCOR, SR, $NR_2$, or $PR_2$, or two X groups can be joined to form OR'O;

R is a linear or branched, cyclic or acyclic, $C_1$-$C_{40}$-alkyl, $C_2$-$C_{40}$ alkenyl, $C_2$-$C_{40}$ alkynyl, $C_6$-$C_{40}$-aryl, $C_7$-$C_{40}$-alkylaryl or $C_7$-$C_{40}$-arylalkyl, optionally comprising at least one heteroatom belonging to groups 13-17 of the Periodic Table of Elements;

R' is a $C_1$-$C_{20}$-alkylidene, $C_6$-$C_{20}$-arylidene, $C_7$-$C_{20}$-alkylarylidene, or $C_7$-$C_{20}$-arylalkylidene radical;

W is an aromatic 5 or 6 membered ring optionally comprising at least one heteroatom belonging to groups 15-16 of the Periodic Table of Elements, wherein the valence of each atom of said 5 or 6 membered ring is substituted with hydrogen, or is optionally substituted with at least one $R^5$;

$R^5$, equal to or different from each other, is a $C_1$-$C_{40}$ hydrocarbon, optionally comprising at least one heteroatom belonging to groups 13-17 of the Periodic Table of Elements;

$R^1$ is a linear $C_1$-$C_{40}$ hydrocarbon, optionally comprising at least one heteroatom belonging to groups 13-17 of the Periodic Table of Elements;

$R^4$ is hydrogen, or a $C_1$-$C_{40}$ hydrocarbon optionally comprising at least one heteroatom belonging to groups 13-17 of the Periodic Table of Elements; and $R^{18}$, equal to or different from each other, are hydrogen or a $C_1$-$C_{40}$ hydrocarbon, optionally comprising at least one heteroatom belonging to groups 13-17 of the Periodic Table of Elements.

12. A bridged metallocene compound of formula (Ib):

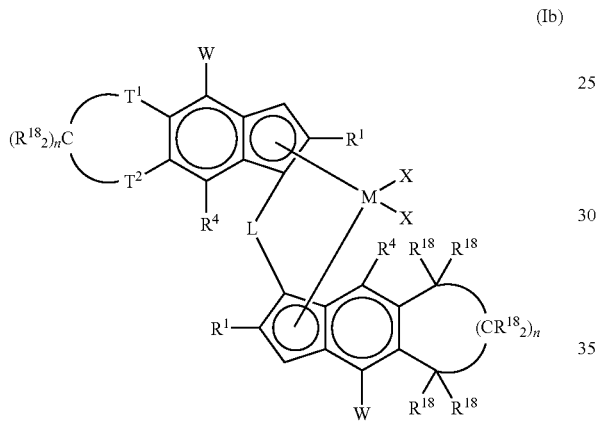

(Ib)

wherein
n is 1 or 2;

M is an atom of a transition metal selected from group 4 or the actinide group in the Periodic Table of Elements;

X, equal to or different from each other, is hydrogen, a halogen, R, OR, $OSO_2CF_3$, OCOR, SR, $NR_2$, or $PR_2$, or two X groups can be joined to form OR'O;

R is a linear or branched, cyclic or acyclic, $C_1$-$C_{40}$-alkyl, $C_2$-$C_{40}$ alkenyl, $C_2$-$C_{40}$ alkynyl, $C_6$-$C_{40}$-aryl, $C_7$-$C_{40}$-alkylaryl or $C_7$-$C_{40}$-arylalkyl, optionally comprising at least one heteroatom belonging to groups 13-17 of the Periodic Table of Elements;

R' is a $C_1$-$C_{20}$-alkylidene, $C_6$-$C_{20}$-arylidene, $C_7$-$C_{20}$-alkylarylidene, or $C_7$-$C_{20}$-arylalkylidene radical;

L is a divalent bridging group selected from a $C_1$-$C_{20}$ alkylidene, a $C_3$-$C_{20}$ cycloalkylidene, a $C_6$-$C_{20}$ arylidene, a $C_7$-$C_{20}$ alkylarylidene, or a $C_7$-$C_{20}$ arylalkylidene, optionally comprising at least one heteroatom belonging to groups 13-17 of the Periodic Table of Elements, or L is a silylidene radical comprising up to 5 silicon atoms;

W is an aromatic 5 or 6 membered ring optionally comprising at least one heteroatom belonging to groups 15-16 of the Periodic Table of Elements, wherein the valence of each atom of said 5 or 6 membered ring is substituted with hydrogen, or is optionally substituted with at least one $R^5$;

$R^5$, equal to or different from each other is a $C_1$-$C_{40}$ hydrocarbon optionally comprising at least one heteroatom belonging to groups 13-17 of the Periodic Table of Elements;

$T^1$ and $T^2$, equal to or different from each other, are oxygen, sulfur, or $C(R^{18})_2$, with the proviso that at least one of $T^1$ and $T^2$ is oxygen or sulfur;

$R^{18}$, equal to or different from each other, are hydrogen or a $C_1$-$C_{40}$ hydrocarbon, optionally comprising at least one heteroatom belonging to groups 13-17 of the Periodic Table of Elements;

$R^1$ is a linear $C_1$-$C_{40}$ hydrocarbon, optionally comprising at least one heteroatom belonging to groups 13-17 of the Periodic Table of Elements; and $R^4$ is hydrogen, or a $C_1$-$C_{40}$ hydrocarbon optionally comprising at least one heteroatom belonging to groups 13-17 of the Periodic Table of Elements.

13. A catalyst system for polymerizing at least one olefin, the catalyst system obtained by contacting:
a bridged metallocene compound of formula (I)

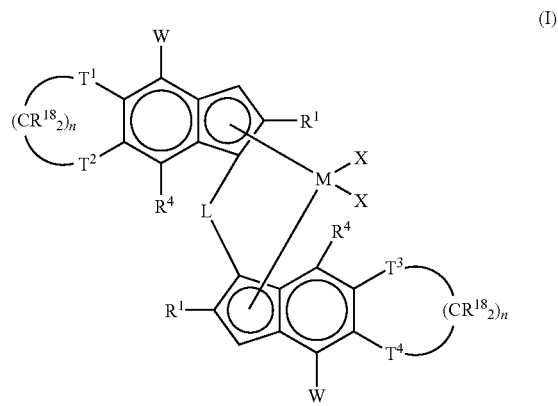

(I)

wherein:
M is an atom of a transition metal selected from group 4 or the actinide group in the Periodic Table of Elements;

X, equal to or different from each other, is hydrogen, a halogen, R, OR, $OSO_2CF_3$, OCOR, SR, $NR_2$, or $PR_2$, or two X groups can be joined to form OR'O;

R is a linear or branched, cyclic or acyclic, $C_1$-$C_{40}$-alkyl, $C_2$-$C_{40}$ alkenyl, $C_2$-$C_{40}$ alkynyl, $C_6$-$C_{40}$-aryl, $C_7$-$C_{40}$-alkylaryl or $C_7$-$C_{40}$-arylalkyl, optionally comprising at least one heteroatom belonging to groups 13-17 of the Periodic Table of Elements;

R' is a $C_1$-$C_{20}$-alkylidene, $C_6$-$C_{20}$-arylidene, $C_7$-$C_{20}$-alkylarylidene, or $C_7$-$C_{20}$-arylalkylidene radical;

L is a divalent bridging group selected from a $C_1$-$C_{20}$ alkylidene, a $C_3$-$C_{20}$ cycloalkylidene, a $C_6$-$C_{20}$ arylidene, a $C_7$-$C_{20}$ alkylarylidene, or a $C_7$-$C_{20}$ arylalkylidene, optionally comprising at least one heteroatom belonging to groups 13-17 of the Periodic Table of Elements, or L is a silylidene radical comprising up to 5 silicon atoms;

$R^1$ is a linear $C_1$-$C_{40}$ hydrocarbon, optionally comprising at least one heteroatom belonging to groups 13-17 of the Periodic Table of Elements;

$T^1$ and $T^2$, equal to or different from each other, are oxygen, sulfur, or $C(R^{18})_2$, with the proviso that at least one of $T^1$ and $T^2$ is oxygen or sulfur;

$R^{18}$, equal to or different from each other, are hydrogen or a $C_1$-$C_{40}$ hydrocarbon, optionally comprising at least one heteroatom belonging to groups 13-17 of the Periodic Table of Elements;

n is 1, 2 or 3;

$T^3$ and $T^4$, equal to or different from each other, are oxygen, sulfur, or $C(R^{18})_2$;

$R^4$ is hydrogen, or a $C_1$-$C_{40}$ hydrocarbon optionally comprising at least one heteroatom belonging to groups 13-17 of the Periodic Table of Elements;

W is an aromatic 5 or 6 membered ring optionally comprising at least one heteroatom belonging to groups 15-16 of the Periodic Table of Elements, wherein the valence of each atom of said 5 or 6 membered ring is substituted with hydrogen, or is optionally substituted with at least one $R^5$; and $R^5$, equal to or different from each other, is a $C_1$-$C_{40}$ hydrocarbon, optionally comprising at least one heteroatom belonging to groups 13-17 of the Periodic Table of Elements;

at least one alumoxane, or a compound capable of forming an alkylmetallocene cation; and optionally an organo aluminum compound.

14. A process for preparing an alpha-olefin polymer comprising, contacting under polymerization conditions, at least one alpha-olefin of formula $CH_2$=CHA, wherein A is hydrogen or a $C_1$-$C_{20}$ alkyl, with a catalyst system comprising:

a bridged metallocene compound of formula (I)

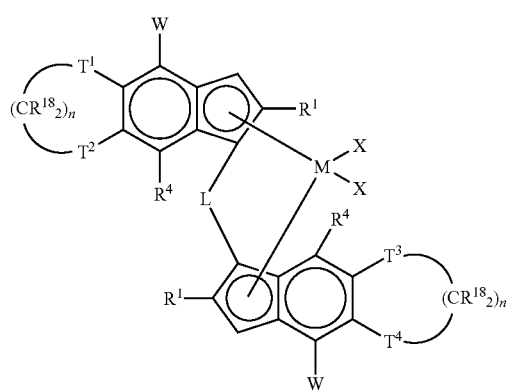

wherein:

M is an atom of a transition metal selected from group 4 or the actinide group in the Periodic Table of Elements;

X, equal to or different from each other, is hydrogen, a halogen, R, OR, $OSO_2CF_3$, OCOR, SR, $NR_2$, or $PR_2$, or two X groups can be joined to form OR'O;

R is a linear or branched, cyclic or acyclic, $C_1$-$C_{40}$-alkyl, $C_2$-$C_{40}$ alkenyl, $C_2$-$C_{40}$ alkynyl, $C_6$-$C_{40}$-aryl, $C_7$-$C_{40}$-alkylaryl or $C_7$-$C_{40}$-arylalkyl, optionally comprising at least one heteroatom belonging to groups 13-17 of the Periodic Table of Elements;

R' is a $C_1$-$C_{20}$-alkylidene, $C_6$-$C_{20}$-arylidene, $C_7$-$C_{20}$-alkylarylidene, or $C_7$-$C_{20}$-arylalkylidene radical;

L is a divalent bridging group selected from a $C_1$-$C_{20}$ alkylidene, a $C_3$-$C_{20}$ cycloalkylidene, a $C_6$-$C_{20}$ arylidene, a $C_7$-$C_{20}$ alkylarylidene, or a $C_7$-$C_{20}$ arylalkylidene, optionally comprising at least one heteroatom belonging to groups 13-17 of the Periodic Table of Elements, or L is a silylidene radical comprising up to 5 silicon atoms;

$R^1$ is a linear $C_1$-$C_{40}$ hydrocarbon, optionally comprising at least one heteroatom belonging to groups 13-17 of the Periodic Table of Elements;

$T^1$ and $T^2$, equal to or different from each other, are oxygen, sulfur, or $C(R^{18})_2$, with the proviso that at least one of $T^1$ and $T^2$ is oxygen or sulfur;

$R^{18}$, equal to or different from each other, are hydrogen or a $C_1$-$C_{40}$ hydrocarbon, optionally comprising at least one heteroatom belonging to groups 13-17 of the Periodic Table of Elements;

n is 1, 2 or 3;

$T^3$ and $T^4$, equal to or different from each other, are oxygen, sulfur, or $C(R^{18})_2$;

$R^4$ is hydrogen, or a $C_1$-$C_{40}$ hydrocarbon optionally comprising at least one heteroatom belonging to groups 13-17 of the Periodic Table of Elements;

W is an aromatic 5 or 6 membered ring optionally comprising at least one heteroatom belonging to groups 15-16 of the Periodic Table of Elements, wherein the valence of each atom of said 5 or 6 membered ring is substituted with hydrogen, or is optionally substituted with at least one $R^5$; and $R^5$, equal to or different from each other, is a $C_1$-$C_{40}$ hydrocarbon, optionally comprising at least one heteroatom belonging to groups 13-17 of the Periodic Table of Elements;

at least one alumoxane, or a compound capable of forming an alkylmetallocene cation; and optionally an organo aluminum compound.

15. The process according to claim 14, wherein the process comprises, contacting under polymerization conditions, propylene with ethylene or at least one alpha olefin of formula $CH_2$=$CHA^1$, wherein $A^1$ is a $C_2$-$C_{20}$ alkyl radical, in presence of a catalyst system for polymerizing at least one olefin, the catalyst system obtained by contacting:

the bridged metallocene compound of formula (I);

at least one alumoxane, or a compound capable of forming an alkylmetallocene cation; and optionally an organo aluminum compound.

16. The process according to claim 14, wherein the process is a multistage polymerization process comprising:

polymerizing propylene, with optionally ethylene or at least one alpha olefin of formula $CH_2$=$CHA^1$, wherein $A^1$ is a $C_2$-$C_{20}$ alkyl radical, in presence of catalyst system obtained by contacting:

the bridged metallocene compound of formula (I);

at least one alumoxane, or a compound capable of forming an alkylmetallocene cation; and optionally an organo aluminum compound; and contacting, under polymerization conditions, propylene with ethylene, or at least one alpha olefin of formula $CH_2$=$CHA^1$, and optionally a non-conjugated diene, in presence of a polymer obtained by polymerizing propylene with optionally ethylene or at least one alpha-olefin of formula $CH_2$=$CHA^1$, optionally in presence of an additional organo aluminum compound;

wherein, the polymer produced by polymerizing propylene with optionally ethylene, or at least one alpha olefin of formula $CH_2$=$CHA^1$, is different from a copolymer produced by contacting propylene with ethylene, or at least one alpha olefin of formula $CH_2$=$CHA^1$, and optionally a non-conjugated diene; the process producing a final polymer product comprising from 2% to 98% by weight of a polymer obtained by polymerizing propylene with optionally ethylene or at least one alpha olefin of formula $CH_2$=$CHA^1$; and from 98% to 2% by weight of a polymer obtained by polymerizing propylene with ethylene, or at least one alpha olefin of formula $CH_2=CHA^1$, and optionally a non-conjugated diene.

17. A ligand of formula (III)

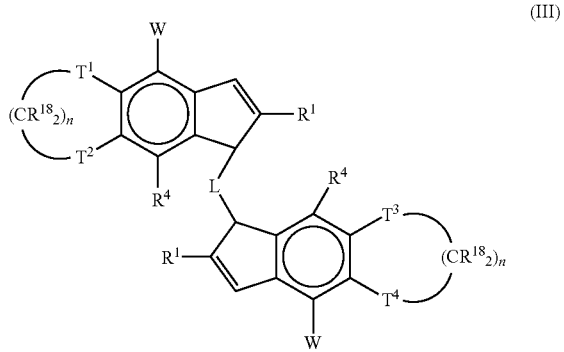

(III)

and double bond isomers thereof,
wherein
n is 1, 2, or 3;
L is a divalent bridging group selected from a $C_1$-$C_{20}$ alkylidene, a $C_3$-$C_{20}$ cycloalkylidene, a $C_6$-$C_{20}$ arylidene, a $C_7$-$C_{20}$ alkylarylidene, or a $C_7$-$C_{20}$ arylalkylidene, optionally comprising at least one heteroatom belonging to groups 13-17 of the Periodic Table of Elements, or L is a silylidene radical comprising up to 5 silicon atoms;

$R^1$ is a linear $C_1$-$C_{40}$ hydrocarbon, optionally comprising at least one heteroatom belonging to groups 13-17 of the Periodic Table of Elements;

$T^1$ and $T^2$, equal to or different from each other, are oxygen, sulfur, or $C(R^{18})_2$, with the proviso that at least one of $T^1$ and $T^2$ is oxygen or sulfur;

$R^{18}$, equal to or different from each other, are hydrogen or a $C_1$-$C_{40}$ hydrocarbon, optionally comprising at least one heteroatom belonging to groups 13-17 of the Periodic Table of Elements;

$T^3$ and $T^4$, equal to or different from each other, are oxygen, sulfur, or $C(R^{18})_2$;

$R^4$ is hydrogen, or a $C_1$-$C_{40}$ hydrocarbon optionally comprising at least one heteroatom belonging to groups 13-17 of the Periodic Table of Elements;

W is an aromatic 5 or 6 membered ring optionally comprising at least one heteroatom belonging to groups 15-16 of the Periodic Table of Elements, wherein the valence of each atom of said 5 or 6 membered ring is substituted with hydrogen, or is optionally substituted with at least one $R^5$; and $R^5$, equal to or different from each other, is a $C_1$-$C_{40}$ hydrocarbon, optionally comprising at least one heteroatom belonging to groups 13-17 of the Periodic Table of Elements.

* * * * *